United States Patent [19]

Lee et al.

[11] Patent Number: 5,750,695
[45] Date of Patent: May 12, 1998

[54] ANTIPARASITIC PARAHERQUAMIDES

[75] Inventors: Byung H. Lee; Michael F. Clothier, both of Kalamazoo, Mich.

[73] Assignee: Pharmacia & Upjohn Company, Kalamazoo, Mich.

[21] Appl. No.: 822,419

[22] Filed: Mar. 21, 1997

Related U.S. Application Data

[62] Division of Ser. No. 670,306, Jun. 27, 1996.

[60] Provisional application No. 60/001,324, Jul. 21, 1995.

[51] Int. Cl.$^6$ .................................... C07D 241/36
[52] U.S. Cl. ...................................... 544/341
[58] Field of Search ................................ 544/341

[56]  References Cited

U.S. PATENT DOCUMENTS

| | | | |
|---|---|---|---|
| 4,866,060 | 9/1989 | Mrozik | 514/250 |
| 4,873,247 | 10/1989 | Goegelman et al. | 514/257 |
| 4,923,867 | 5/1990 | Biizzard et al. | 514/250 |
| 4,978,656 | 12/1990 | Blizzard et al. | 514/63 |

FOREIGN PATENT DOCUMENTS

| | | |
|---|---|---|
| 390532 | 10/1990 | European Pat. Off. |
| WO 91/0996 | 7/1991 | WIPO |
| WO91/09961 | 7/1991 | WIPO |
| WO 92/00300 | 1/1992 | WIPO |
| WO 92/22555 | 12/1992 | WIPO |
| WO92/22555 | 12/1992 | WIPO |
| WO94/29319 | 12/1994 | WIPO |

OTHER PUBLICATIONS

Blanchflower et al., Journal of Antibiotics, vol. 46, No. 9, pp. 1335–1363, 1993.

Blizzard et al., Tetrahedron Lett. (1991), 32(22), 2441–4, 1991.

Schaeffer et al., Biochem. Pharmacol. (1992), 43(4), 679–84, 1992.

Polonsky, J., et al., *J. Chem. Soc. Chem. Comm.*, pp. 601–602 (1980).

Prange, T., et al., *Tetrahedron Letters*, 22, pp. 1977–1980 (1981).

Yamazaki, M., et al., *Tetrahedron Letters*, 22, pp. 135–136 (1981).

Liesch, J.M., et al., *J. Antib.*, 43, pp. 1380–1386 (1990).

Blanchflower, S.E., et al., *J. Antib.*, 44, pp. 492–497 (1991).

CA:vol. 118, No. 19, (1993) 192076d.

*Primary Examiner*—Mukund J. Shah
*Assistant Examiner*—Bruck Kifle
*Attorney, Agent, or Firm*—Bruce Stein

[57]  ABSTRACT

The present invention includes various substituted and paraherquamides, exemplified by the 14-hydroxy-2-deoxoparaherquamide B of formula (XXV)

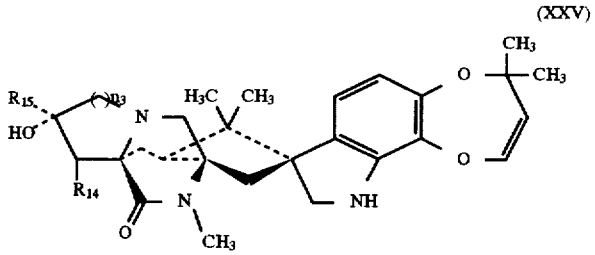

which are useful as antiparasitic agents.

9 Claims, No Drawings

ANTIPARASITIC PARAHERQUAMIDES

CROSS-REFERENCE TO RELATED APPLICATIONS

The present patent application is a divisional application of U.S. patent application Ser. No. 08/670,306 filed Jun. 27, 1996 which is a continuation-in-part patent application of U.S. patent application Ser. No. 60/001,324 filed Jul. 21, 1995.

BACKGROUND OF THE INVENTION

1. Field of the Invention

The present invention is substituted marcfortines and paraherquamides which are useful as antiparasitic agents.

2. Description of the Related Art

The marcfortines are known compounds, see *Journal of the Chemical Society Chemical Communications*, 601–602 (1980) for Marcfortine A and *Tetrahedron Letters*, 22, 1977–1980 ((1981) for Marcfortines B and C. These compounds are fungal metabolites of *Penicillium roqueforti*. The marcfortines are structurally related to the paraherquamides which are also known compounds.

The paraherquamides are disclosed in *Tetrahedron Letters*, 22, 135–136 (1981), and *Journal of Antibiotics*, 44, 492–497 (1991). U.S. Pat. Nos. 4,866,060 and 4,923,867 disclose the use of the marcfortines A, B, and C, and certain derivatives thereof as useful for the treatment and prevention of parasitic diseases in animals.

WO 92/22555 (published 23 Dec. 1992) generically describes a marcfortine or paraherquamide derivative (i.e. partial formula (III) substituted at position 14 with methyl or methyl and hydroxy, however no description of how to prepare such 14-methyl-14-hydroxymarcfortine compounds is provided.

The *Journal of Antibiotics*, 43, 1380–1386 (1990) discloses Paraherquamide A which has the following structure:

Marcfortine A has the following structure:

Marcfortine B has the following structure:

Marcfortine C has the following structure:

Marcfortine D has the following structure:

WO 91/09961 (published 11 Jul. 1991) discloses various derivatives of marcfortine and paraherquamide, and 12a-N-oxides thereof, as well as the production the production of VM 29919 (paraherquamide) and VM 55596 (the 12a-N-oxide of paraherquamide) inter alia from Penicillium Sp. IMI 332995.

U.S. Pat. No. 4,873,247 discloses derivatives of paraherquamide and a strain of *Penicillium charlessi* MF 5123 (ATCC 20841) for the production of paraherquamide. U.S. Pat. No. 4,978,656 (as well as EP 390532-A, EP-301742-A) discloses various synthetic derivatives of paraherquamide as well as the production of paraherquamide from *Penicillium charlessi* MF 5123 (ATCC 20841).

International Publication WO 92/22555 (published 23 Dec. 1992) generically discloses 14α-hydroxymarcfortine compounds and a process which uses the 14-hydroxy-14-methylmarcfortine compounds for the production of antiparasitic drugs. However, no enabling description of any means of preparation of 14α-hydroxymarcfortine or 14α-hydroxy-14β-methylmarcfortine compounds is provided.

International Publication WO94/29319 discloses various 14-substituted marcfortines and derivatives thereof.

The 15-alkyl-14-hydroxy compounds (III) where $n_1$ is 0 are known, see International Publication WO94/29319.

SUMMARY OF INVENTION

Disclosed are 15-alkyl-14-hydroxy compounds of formula (III) where $n_1$ is 1 thru 3, the N-oxides and pharmaceutically acceptable salts thereof.

Also disclosed are fluoro compounds of formula (VIII) where $n_2$ is 0 thru 3 the N-oxides and pharmaceutically acceptable salts thereof.

Further disclosed are 15-alkyl-16-hydroxy compounds of formula (X) where $n_1$ is 0 thru 3 the N-oxides and pharmaceutically acceptable salts thereof.

Additionally disclosed are paraherquamide B compounds of formula (XIII) where $n_1$ is 0 thru 3 the N-oxides and pharmaceutically acceptable salts thereof.

Disclosed is 14,15-Dehydro-16-oxoparaherquamide B.

Also disclosed are 2-deoxo-15-alkyl compounds of formula (XXI) where $R_{14}$ is —H or $C_1$-$C_4$ alkyl and where $R_{15}$ is —H or $C_1$-$C_4$ alkyl the N-oxides and pharmaceutically acceptable salts thereof.

Further disclosed is the 2-deoxo compound of formula (XXIII) which is 2-desoxomarcfortine A and pharmaceutically acceptable salts thereof.

Additionally disclosed are 14-hydroxy-2-deoxoparaherquamide compounds of formula (XXV) the N-oxides and pharmaceutically acceptable salts thereof.

Disclosed are compounds selected from the group consisting of 15α-ethyl-14α-Hydroxy-17-oxomarcfortine A, 14α-hydroxy-15α-vinyl-17-oxomarcfortine A, 14α-hydroxy-15α-(1',2'-dihydroxyethyl)-17-oxomarcfortine A, 14α-hydroxy-15α-hydroxymethyl-17-oxomarcfortine A, 15α-fluoromethyl-14α-hydroxy-17-oxomarcfortine A, 14,15-dehydro-15-methylmarcfortine A, 14α-hydroxy-16, 17-dioxo-15α-methylmarcfortine A, 14α-hydroxy-16-oxo-15α-methylparaherquamide B, 16,17-dioxomarcfortine A, 16-oxoparaherquamide B (XVI), 14α-hydroxy-15α-methyl-17-oxomarcfortine.

Disclosed are 1,2-dehydro compounds (XXIX).

Also disclosed are 2-alkyl-2-desoxo compounds (XXXI).

DETAILED DESCRIPTION OF THE INVENTION

The claimed compounds are prepared by processes known to those skilled in the art from starting materials known to those skilled in the art or which can readily be prepared from known compounds by methods known to those skilled in the art. Known chemistry is used on known starting materials in novel sequences to produce the novel compounds of the invention.

CHART A discloses the preferred process to produce the 15-alkyl-14-hydroxy compounds (III). The starting 14-hydroxy-α,β-unsaturated compound (I) is known, see International Publication WO94/29319. The 14-hydroxy-α, β-unsaturated compounds (I) can be transformed to the corresponding 15-alkyl-17-oxo compounds (II) by reaction with an alkylating agents such as a Grignard reagent or alkylcuprates; it is preferred that the alkylating reagent be a Grignard reagent of the formula $CH_3$—$(CH_2)_{n1}$—Mg—$X_o$, where $n_1$ is 0 thru 3 and $X_o$ is halogen. It is preferred that $n_1$ is 1 and $X_o$ is —Br. The preferred process is to react the 14-hydroxy-α,β-unsaturated compound (I) with ethylmagnesium bromide and copper (I) iodide under standard 1,4-addition conditions to produce the 15-alkyl-17-oxo compounds (II). The 15-alkyl-17-oxo compounds (II) are then reduced my means known to those skilled in the art for reduction of a carbonyl group to an alkylene moiety such as reduction with borane dimethyl sulfide complex or other reducing agents such as borane THF complex or lithium aluminum hydride. It is preferred that borane dimethyl sulfide complex be used for the reduction. With the 15-alkyl-14-hydroxy compounds (III), it is preferred that $n_1$ is 1. The 15-alkyl-14-hydroxy compounds (III) where $n_1$ is 0 are known, see International Publication WO94/29319.

CHART B discloses a process to produce the fluoro compounds of formula (VIII). The 14-hydroxy-α,β-unsaturated (I) starting material is transformed to the corresponding unsaturated compound (IV) by a Grignard addition similar to that used to alkylate the 14-hydroxy-α,β-unsaturated compound (I) in CHART A but now using $CH_2$=CH—$(CH_2)_{n2}$—Mg—$X_o$/copper iodide where $n_2$ is 0 thru 3 in place of $CH_3$—$(CH_2)_{n1}$—Mg—$X_o$ (CHART A). The unsaturated compound (IV) is then transformed to the corresponding dihydroxy compound (V) by oxidizing the double bond of the unsaturated portion of the $C_{15}$ side chain by reaction with an oxidizing agent such as osium tetroxide (catalyic) and 4-methylmorpholine N-oxide; it is preferred that the oxidizing agent is osium tetroxide and 4-methylmorpholine N-oxide. The dihydroxy compounds (V) are then transformed to the corresponding hydroxyalkyl compounds (VI) by oxidation followed by reduction. It is preferred that the oxidizing agent be sodium periodate and the reducing agent be sodium borohydride. The hydroxyalkyl compounds (VI) are transformed to the corresponding fluoro-oxo compounds (VII) by reaction with a fluorinating reagent such as tetrabutylammonium fluoride and p-toluenesulfonyl fluoride. The endocyclic double bond of the fluoro-oxo compounds (VII) is reduced by known methods, preferably borane-tetrahydrofuran complex to give the desired fluoro compound (VIII). With the fluoro compounds (VIII), it is preferred that $n_2$ is 1.

CHART C discloses a process to produce 15-alkyl-16-hydroxy compounds (X). The 14-hydroxyl group is first removed to give a 14,15-dehydro functionality by a well known method using diethylaminosulfur trifluoride (DAST) to give the $\Delta^{14}$-15-alkyl compounds (IX). The $\Delta^{14}$-15-alkyl compounds (IX) are hydroxylated to give the desired 15-alkyl-16-hydroxy compounds (X) by reaction with a hydroxylating agent, preferably selenium dioxide refluxing in an inert solvent such as p-dioxane. With the 15-alkyl-16-hydroxy compounds (X), it is preferred that $n_1$ is 0.

CHART D discloses a process to produce the 15-alkyl paraherquamide B compounds (XIII). The 15-alkyl-14-hydroxy starting compounds (III) are oxidized to the corresponding 15-alkyl-16,16-dioxo Marcfortine A compounds (XI) by reaction with oxygen in the presence of a catalyst such as platinum on carbon. The 15-alkyl-16,17-dioxo Marcfortine A compounds (XI) then have the six member dioxo ring reduced to a five member ring produce the 15-alkyl-16-oxo paraherquamide B compounds (XII) by treatment with a peracid preferably m-chloroperbenzoic acid. The 15-alkyl-16-oxo paraherquamide B compounds (XII) then have the 16-oxo group removed by use of a reducing agent, preferably lithium aluminum hydride/aluminum chloride to give the desired 15-alkyl paraherquamide B compounds (XIII). With the 15-alkyl paraherquamide B compounds (XIII), it is preferred that $n_1$ is 0.

CHART E discloses processes to produce various oxo compounds which are 16,17-dioxomarcfortine A (XV), 16-oxoparaherquamide B (XVI) and 14,15-dehydro-16-oxoparaherquamide B (XVII), by the processes of EXAMPLES 13 and 14.

CHART F discloses processes to produce 2-deoxo-14-hydroxy compounds (XXI) starting with 14-hydroxy-α,β-unsaturated ketones (XVIII) where $R_{14}$ is —H or $C_1$-$C_4$ alkyl and where $R_{15}$ is —H or $C_1$-$C_4$ alkyl. The 14-hydroxy-α,β-unsaturated amides (XVIII) have the $\Delta^{15}$-double bond reduced by reaction with the appropriate lithium reagent $R_{15}$—Li in the presence of lithium bromide to give the 14-hydroxy-17-oxo compounds (XIX). The $C_{15}$-position can be alkylated during this reaction if so desired. The 14-hydroxy-17-oxo compounds (XIX) next have the 17-oxo group reduced by means of borane dimethyl sulfide complex (as previously described in CHART A), see EXAMPLE 15. This reduction produces the 14-hydroxy compound (XX) as well as the compound where both the 2- and 17-carbonyl groups are reduced, the desired 2-deoxo-14-hydroxy (XXI) compound.

CHART G discloses a process to produce the 2-deoxo compounds (XXIII), see EXAMPLE 16.

CHART H discloses a process to produce the corresponding 14-hydroxy 2-deoxoparaherquamides (XXV).

Alternatively, and preferably, 2-desoxomarcfortine (XXIII), 14-hydroxy-2-desoxoparaherquamide B and 14-hydroxymarcfortine A (XXV) derivatives can be prepared in 40–70% yield by the process set forth in CHART O. CHART O discloses that the amide (XXVI) is reacted with an appropriate alkyl chloroformate or anhydride derivative by treatment with either potassium hydride or sodium hydride to provide the corresponding imide (XXVII), which is reduced with sodium borohydride to give the corresponding 2-hydroxy compound (XXVIII). In the imide (XXVII) the nitrogen at N-1 must be protected (see $R_{17}$ of formula XXVII) as is known to those skilled in the art until after the reduction of of the C-2 carbonyl. Preferred protecting groups include phenyl, 4-nitrophenyl and t-butylfluorenylmethyl. The 2-hydroxy compound (XXVIII) is then deprotected by various methods known to those skilled in the art to give the corresponding 1,2-dehydro compound (XXIX), which can be reduced with sodium borohydride to give the corresponding 2-desoxomarcfortine (XXIII), 14-hydroxy-2-desoxoparaherquamide B and 14-hydroxymarcfortine A (XXV) in 40–70% overall yield. When $R_{17}$ is t-butyl, a shorter way of obtaining the 2-desoxomarcfortine (XXIII), 14-hydroxy-2-desoxoparaherquamide B and 14-hydroxymarcfortine A (XXV) is by reacting the imide (XXVII) with sodium borohydride refluxing in glyme or diglyme.

The 2-alkyl-2-desoxoparaquamide A (XXXI) is obtained from the corresponding 1,2-dehydromarcfortine A (XXIX) by reaction with the appropriate alkyl lithium reagent as is known to those skilled in the art.

The ANTIPARASITIC COMPOUNDS refers to and includes 15-alkyl-14-hydroxy compounds (III), fluoro compounds (VIII), 15-alkyl-16-hydroxy compounds (X), 15-alkyl paraherquamide B (XIII), 2-deoxo-14-hydroxy compounds (XXI), 2-desoxomarcfortine (XXIII), 14-hydroxy-2-desoxoparaherquamide B and 14-hydroxymarcfortine A (XXV), 14,15-Dehydro-16-oxoparaherquamide B (XVII), 1,2-dehydro compound (XXIX) and 2-alkyl-2-desoxo compound (XXXI), the N-oxides thereof and pharmaceutically acceptable salts thereof where such exist.

The ANTIPARASITIC COMPOUNDS are amines, and as such form acid addition salts when reacted with acids of sufficient strength. Pharmaceutically acceptable salts include salts of both inorganic and organic acids. The pharmaceutically acceptable salts are preferred over the corresponding free amines since they produce compounds which are more water soluble and more crystalline. The preferred pharmaceutically acceptable salts include salts of the following acids methanesulfonic, hydrochloric, hydrobromic, sulfuric, phosphoric, nitric, benzoic, citric, tartaric, fumaric, maleic, $CH_3-(CH_2)_n-COOH$ where n is 0 thru 4, $HOOC-(CH_2)_n-COOH$ where n is as defined above.

The ANTIPARASITIC COMPOUNDS are amines and by reacting them with peracids such as m-chloroperbonzoic acid the corresponding 12a-N-oxides are obtained as is known to those skilled in the art.

The ANTIPARASITIC COMPOUNDS of this invention are unexpectedly potent antiparasitic agents against endo and ecto parasites, particularly helminths and arthropods, which cause numerous parasitic diseases in humans, animals, and plants.

Parasitic diseases may be caused by either endoparasites or ectoparasites. Endoparasites are those parasites which live inside the body of the host, either within an organ (such as the stomach, lungs, heart, intestines, etc.) or simply under the skin. Ectoparasites are those parasites which live on the outer surface of the host but still draw nutrients from the host.

The endoparasitic diseases generally referred to as helminthiasis are due to infection of the host with parasitic worms known as helminths. Helminthiasis is a prevalent and serious worldwide economic problem due to infection of domesticated animals such as swine, sheep, horses, cattle, goats, dogs, cats, and poultry. Many of these infections are caused by the group of worms described as nematodes which cause diseases in various species of animals throughout the world. These diseases are frequently serious and can result in the death of the infected animal. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris, and Parascaris. Many parasites are species specific (infect only one host) and most also have a preferred site of infection within the animal. Thus Haemonchus and Ostertagia primarily infect the stomach while Nematodirus and Cooperia mostly attack the intestines. Other parasites prefer to reside in the heart, eyes, lungs, blood vessels, and the like while still others are subcutaneous parasites. Helminthiasis can lead to weakness, weight loss, anemia, intestinal damage, malnutrition, and damage to other organs. If left untreated these diseases can result in the death of the animal.

Infections by ectoparasitic arthropods such as ticks, mites, lice, stable flies, hornflies, blowflies, fleas, and the like are also a serious problem. Infection by these parasites results in loss of blood, skin lesions, and can interfere with normal eating habits thus causing weight loss. These infections can also result in transmission of serious diseases such as encephalitis, anaplasmosis, swine pox, and the like which can be fatal.

Animals may be infected by several species of parasite at the same time since infection by one parasite may weaken the animal and make it more susceptible to infection by a second species of parasite. Thus a compound with a broad spectrum of activity is particularly advantageous in the treatment of these diseases. The ANTIPARASITIC COMPOUNDS have unexpectedly high activity against these parasites, and in addition, are also active against Dirofilaria in dogs, Nematospiroides and Syphacia in rodents, biting insects and migrating dipterous larvae such as Hypoderma sp. in cattle, and Gastrophilus in horses.

The ANTIPARASITIC COMPOUNDS are also useful against endo and ecto parasites which cause parasitic diseases in humans. Examples of such endoparasites which infect man include gastro intestinal parasites of the genera Ancylostoma, Necator, Ascaris, Strongyloides, Trichinella, Capillaria, Trichuris, Enterobius, and the like. Other endoparasites which infect man are found in the blood or in other organs. Examples of such parasites are the filarial worms Wucheria, Brugia, Onchocerca, and the like as well as extra intestinal stages of the intestinal worms Strongylides and Trichinella. Ectoparasites which parasitize man include arthropods such as ticks, fleas, mites, lice, and the like and, as with domestic animals, infections by these parasites can result in transmission of serious and even fatal diseases. The ANTIPARASITIC COMPOUNDS are active against these endo and ecto parasites and in addition are also active against biting insects and other dipterous pests which annoy humans. The ANTIPARASITIC COMPOUNDS when administered orally or parenterally are administered at a dosage rate of from 0.05 to 20 mg/kg of animal body weight.

The ANTIPARASITIC COMPOUNDS are also useful against common household pests such as Blatella sp. (cockroach), Tineola sp. (clothes moth), Attagenus sp. (carpet beetle), *Musca domestica* (housefly) and against *Solenopsis Invicta* (imported fire ant).

The ANTIPARASITIC COMPOUNDS are furthermore useful against agricultural pests such as aphids (Acyrthiosiphon sp.), locusts, and boll weevils as well as against insect pests which attack stored grains such as Tribolium sp. and against immature stages of insects living on plant tissue. The ANTIPARASITIC COMPOUNDS are also useful as a nematocide for the control of soil nematodes which may be agriculturally important.

For use as an antiparasitic agent in animals the ANTIPARASITIC COMPOUNDS may be administered internally either orally or by injection, or topically as a liquid drench or as a shampoo.

For oral administration, the ANTIPARASITIC COMPOUNDS may be administered in capsule, tablet, or drench bolus form or alternatively they can be mixed in the animals feed. The capsules, tablets, and drenches boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, suspending agents, and/or binders such that a uniform mixture solution or suspension is obtained. An inert ingredient is one that will not react with the ANTIPARASITIC COMPOUNDS and which is non toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the ANTIPARASITIC COMPOUNDS with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5.0% by weight of the active ingredient.

The ANTIPARASITIC COMPOUNDS may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 20% by weight of the active ingredient.

Topical application of the ANTIPARASITIC COMPOUNDS is possible through the use of a liquid drench or a shampoo containing the ANTIPARASITIC COMPOUNDS as an aqueous solution or suspension. These formulations generally contain a suspending agent such as bentonite and normally will also contain an antifoaming agent. Formulations containing from 0.005 to 20% by weight of the active ingredient are acceptable. Preferred formulations are those containing from 0.5 to 5% by weight of the ANTIPARASITIC COMPOUNDS.

The ANTIPARASITIC COMPOUNDS are primarily useful as antiparasitic agents for the treatment and/or prevention of helminthiasis in domestic animals such as cattle, sheep, horses, dogs, cats, goats, swine, and poultry. They are also useful in the prevention and treatment of parasitic infections of these animals by ectoparasites such as ticks, mites, lice, fleas and the like. They are also effective in the treatment of parasitic infections of humans. In treating such infections the ANTIPARASITIC COMPOUNDS may be used individually or in combination with each other or with other unrelated antiparasitic agents. The dosage of the ANTIPARASITIC COMPOUNDS required for best results depends on several factors such as the species and size of the animal, the type and severity of the infection, the method of administration and the particular ANTIPARASITIC COMPOUNDS used. Oral administration of the ANTIPARASITIC COMPOUNDS a dose level of from 0.005 to 50 mg per kg of animal body weight either in a single dose or in several doses spaced a few days apart, generally gives good results. A single dose of one of the ANTIPARASITIC COMPOUNDS normally gives excellent control however repeat doses may be given to combat re-infection or for parasite species which are unusually persistent. The techniques for administering the ANTIPARASITIC COMPOUNDS to animals are known to those skilled in the veterinary field.

The ANTIPARASITIC COMPOUNDS may also be used to combat agricultural pests which attack crops either in the field or in storage. The ANTIPARASITIC COMPOUNDS are applied for such uses as sprays, dusts, emulsions and the like either to the growing plants or the harvested crops. The techniques for applying the ANTIPARASITIC COMPOUNDS in this manner are known to those skilled in the agricultural arts.

The exact dosage and frequency of administration depends on the particular ANTIPARASITIC COMPOUNDS used, the particular condition being treated, the severity of the condition being treated, the age, weight, general physical condition of the particular patient, other medication the individual may be taking as is well known to those skilled in the art and can be more accurately determined by measuring the blood level or concentration of the ANTIPARASITIC COMPOUNDS in the patient's blood and/or the patient's response to the particular condition being treated.

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3$—$C(=Z_1)$ H. Groups $R_i$ and $R_j$ would represent monovalent variable substituents if attached to the formula $CH_3$—$CH_2$—$C(R_i)$ $(R_j)$—H. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3$—O—$CH_2$—$CH(R_i)$—$CH_3$ represents a 2-substituted-1-methoxypropane compound. In a similar fashion, the symbol "=" represents a double bond, e.g., $CH_2$=$C(R_i)$—O—$CH_3$, and the symbol "≡" represents a triple bond, e.g., HC≡C—$CH(R_i)$—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by N*=$C(CH_3)$—CH=CCl—CH=C*H with the convention that the atoms marked with an asterisk (*) are bonded to each other resulting in the formation of a ring. Likewise, the cyclic molecular fragment, 4-(ethyl)-1-piperazinyl can be represented by —N*—$(CH_2)_2$—$N(C_2H_5)$—$CH_2$—C*$H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —$C(X_1)(X_2)$— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha ($\alpha$) configuration and is identified by a broken, dashed or dotted line attachment to the carbon atom, i.e., by the symbol " - - - " or " . . . ". The corresponding substituent attached "above" ($X_2$) the other ($X_1$) is identified as being in the beta ($\beta$) configuration and is indicated by an unbroken line attachment to the carbon atom.

When a variable substituent is bivalent, the valences may be taken together or separately or both in the definition of the variable. For example, a variable $R_i$ attached to a carbon atom as —$C(=R_i)$— might be bivalent and be defined as oxo (thus forming a carbonyl group (—CO—) or as two separately attached monovalent variable substituents $\alpha$-$R_{i\text{-}j}$ and $\beta$-$R_{i\text{-}k}$. When a bivalent variable, $R_i$, is defined to consist of two monovalent variable substituents, the convention used to define the bivalent variable is of the form "$\alpha$-$R_{i\text{-}j}$:$\beta$-$R_{i\text{-}k}$" or some variant thereof. In such a case both $\alpha$-$R_{i\text{-}j}$ and $\beta$-$R_{i\text{-}k}$ are attached to the carbon atom to give —$C(\alpha$-$R_{i\text{-}j})(\beta$-$R_{i\text{-}k})$—. For example, when the bivalent variable $R_6$, —$C(=R_6)$— is defined to consist of two monovalent variable substituents, the two monovalent variable substituents are $\alpha$-$R_{6\text{-}1}$:$\beta$-$R_{6\text{-}2}$, . . . $\alpha$-$R_{6\text{-}9}$:$\beta$-$R_{6\text{-}10}$, etc, giving —$C(\alpha$-$R_{6\text{-}1})(\beta$-$R_{6\text{-}2})$—, . . . —$C(\alpha$-$R_{6\text{-}9})(\beta$-$R_{6\text{-}10})$—, etc. Likewise, for the bivalent variable $R_{11}$, —$C(=R_{11})$—, two monovalent variable substituents are $\alpha$-$R_{11\text{-}1}$:$\beta$-$R_{11\text{-}2}$. For a ring substituent for which separate $\alpha$ and $\beta$ orientations do not exist (e.g. due to the presence of a carbon carbon double bond in the ring), and for a substituent bonded to a carbon atom which is not part of a ring the above convention is still used, but the $\alpha$ and $\beta$ designations are omitted.

Just as a bivalent variable may be defined as two separate monovalent variable substituents, two separate monovalent variable substituents may be defined to be taken together to form a bivalent variable. For example, in the formula —$C_1(R_i)H$—$C_2(R_j)H$— ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation " . . . $R_i$ and $R_j$ are taken together to form —$CH_2$—$CH_2$—O—CO— . . . " means a lactone in which the carbonyl is bonded to $C_2$. However, when designated " . . . $R_j$ and $R_i$ are taken together to form —CO—O—$CH_2$—$CH_2$— the convention means a lactone in which the carbonyl is bonded to $C_1$.

The carbon atom content of variable substituents is indicated in one of two ways. The first method uses a prefix to the entire name of the variable such as "$C_1$-$C_4$", where both "1" and "4" are integers representing the minimum and maximum number of carbon atoms in the variable. The prefix is separated from the variable by a space. For example, "$C_1$-$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$-$C_4$ alkoxycarbonyl describes a group $CH_3$—$(CH_2)_n$—O—CO— where n is zero, one or two. By the second method the carbon atom content of only each portion of the definition is indicated separately by enclosing the "$C_i$-$C_j$" designation in parentheses and placing it immediately (no intervening space) before the portion of the definition being defined. By this optional convention ($C_1$-$C_3$)alkoxycarbonyl has the same meaning as $C_2-C_4$ alkoxycarbonyl because the "$C_1-C_3$" refers only to the carbon atom content of the alkoxy group. Similarly while both $C_2-C_6$ alkoxyalkyl and $(C_1-C_3)$ alkoxy$(C_1-C_3)$alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. DEFINITIONS

ANTIPARASITIC COMPOUNDS refers to and includes
15-alkyl-14-hydroxy compounds (III),
fluoro compounds (VIII),
15-alkyl-16-hydroxy compounds (X),
15-alkyl paraherquamide B (XIII),
2-deoxo-14-hydroxy compounds (XXI),
2-deoxo compounds (XXIII),
14-hydroxy 2-deoxoparaherquamide compounds (XXV),
14,15-Dehydro-16-oxoparaherquamide B (XVII),
1,2-dehydro compound (XXIX) and
2-Alkyl-2-desoxo compound (XXXI) N-oxides thereof and pharmaceutically acceptable salts thereof where such exist.

All temperatures are in degrees Centigrade.

THF refers to tetrahydrofuran.

Saline refers to an aqueous saturated sodium chloride solution.

Chromatography (column and flash chromatography) refers to purification/separation of compounds expressed as (support, eluent). It is understood that the appropriate fractions are pooled and concentrated to give the desired compound(s).

NMR refers to nuclear (proton) magnetic resonance spectroscopy, chemical shifts are reported in ppm (δ) downfield from tetramethylsilane.

MS refers to mass spectrometry expressed as m/e, mz or mass/charge unit. $[M+H]^+$ refers to the positive ion of a parent plus a hydrogen atom. EI refers to electron impact. CI refers to chemical ionization. FAB refers to fast atom bombardment.

HRMS refers to high resolution mass spectrometry.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

Pharmaceutically acceptable anion salts include salts of the following acids methanesulfonic, hydrochloric, hydrobromic, sulfuric, phosphoric, nitric, benzoic, citric, tartaric, fumaric, maleic, $CH_3-(CH_2)_n-COOH$ where n is 0 thru 4, $HOOC-(CH_2)n-COOH$ where n is as defined above.

When solvent pairs are used, the ratios of solvents used are volume/volume (v/v).

When the solubility of a solid in a solvent is used the ratio of the solid to the solvent is weight/volume (wt/v).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Procedure No. 1

Production and Isolation of Marcfortine A Seed Fermentation Process

Seed fermentations are inoculated using agar plugs of isolate Penicillium sp. UC 7780 (NRRL 18887) stored over liquid nitrogen. Three plugs are thawed and used as inoculum. GS-7 is composed of glucose and cottonseed flour (sold under the trademark "Pharmamedia" by Traders Protein, Procter & Gamble Oilseed Products Co., Memphis, Tenn., U.S.A.). Unsupplemented tap water is used to hydrate the medium components and the medium is adjusted to pH=7.2 with ammonium hydroxide. The medium is dispensed into unbaffled closed-system flasks at 300 ml pper 1000 ml flask, and sterilized by autoclaving at 121° for 30 minutes. Each closed-system flask containing 300 ml of GS-7 medium is inoculated with three agar plugs of Penicillium sp. UC 7780 (NRRL 18887) and shaken on a rotary shaker at 250 rpm for 36 hr at 22°.

Secondary Seed Fermentation Process

The mature seed cultures are used as inoculum for the secondary medium at a 0.3% seed rate. The secondary medium is composed of glucose monohydrate (sold as under the trademark Cerelose by C.P.C. International) 25 g, cottonseed flour (sold under the trademark "Pharmamedia") 25 g, $MgCl_2.6H_2O$ 329.8 mg, $MnSO_4.H_2O$ 11.4 mg, $FeSO_4.7H_2O$ 3.2 mg, $Na_2MoO_4.2H_2O$ 1.8 mg, $CaCl_2.2H_2O$ 367.6 mg NaCl 84.2 mg, KCl 5.8 mg, $ZnSO_4.7H_2O$ 0.1 mg, $CoCl_2.6H_2O$ 0.1 mg, $CuSO_4.5H_2O$ 3.1 mg, and silicone antifoam (sold under the trademark SAG-471 Antifoam) 0.5 ml per liter of reverse-osmosis grade water. Medium components sufficient for 200 liters of secondary seed medium are hydrated in reverse-osmosis grade water to a q.s. volume of 190 liters in a 250-L fermentor. After formulation, the pH of the medium is adjusted to pH 7.2 with $NH_4OH$, and then the medium is sterilized at 121° C. for 30 minutes. Two closed-system flasks of the mature primary-seed culture are used as inoculum at a 0.3% seed rate. The secondary seed culture is incubated at at 22° C., with 125 slm aeration, 5 psig backpressure, and 250 rpm for 36 hours.

Production Fermentation Process

The production medium is composed of beet molasses 50 g, fish meal (sold under the trademark Menhaden Select Fish Meal) 16 g, yeast extract (sold under the trademark Fidco) 10 g, $MgCl_2.6H_2O$ 329.8 mg, $MnSO_4.H_2O$ 11.4 mg, $FeSO_4.7H_2O$ 3.29 mg, $Na_2MoO_4.2H_2O$ 1.8 mg, $CaCl_2.2H_2O$ 367.6 mg, NaCl 84.2 mg, KCl 5.8 mg, $ZnSO_4.7H_2O$ 0.1 mg, $CoCl_2.6H_2O$ 0.1 mg, $CuSO_4.5H_2O$ 3.1 mg, and silicone antifoam (sold under the trademark SAG-471 Antifoam) 0.5 ml per liter of reverse-osmosis grade water.

Medium components sufficient for 5,000 liters of medium are hydrated in reverse-osmosis grade water to a q.s. volume of 4,700 liters in a 5,000 L fermentor. After formulation, the pH of the medium is adjusted to pH 7.0 with KOH, and then the medium is sterilized at 123° C. for 30 minutes. The mature secondary-seed culture is used as inoculum at a 1.0% seed rate. The culture is incubated at 22° C., with 2,500 slm aeration, 5 psig backpressure, and 250 rpm for 96 hours.

Isolation of Marcfortine A

The 4900 L fermentation volume is harvested by passing through a high shear mixer to the harvest vessel. Following transfer, 4% wt./v. of diatomaceous earth and ½ volume of methylene chloride are added. The harvest solution is then filtered using a filter press. The filter cake is washed 2 times with a 10% volume of methylene chloride.

The filtrate obtained is decanted to remove the water (aqueous) phase. The remaining product-rich methylene chloride phase is then concentrated to a volume of 44 L. The concentrate is then polished using a 20% concentrate volume (9 L) of methylene chloride and diatomaceous earth over a filter.

The 53 L polished concentrate is further purified to separate Marcfortine A from other components by silica gel chromatography and crystallization.

Before chromatography, the polished concentrate is divided into four approximately equal aliquots. Each aliquot is chromatographed over a newly packed 9" diameter column prepared from 25 Kg of dry silica gel (bed volume 59 L). The loaded columns are eluted with 120 L of 10% acetone in methylene chloride, 120 L of 20% acetone in methylene chloride, 120 L of 30% acetone in methylene chloride, 160 L of 40% acetone in methylene chloride, and 130 L of acetone collecting the 30 and 40% eluates as 20 L fractions. Eluates are monitored by TLC, using for example a solvent system comprised of 6% isopropanol and 0.3% ammonium hydroxide in methylene chloride to develop Whatman LK6DF silica gel plates. Fractions of Marcfortine A (containing a small amount of Marcfortine D which co-chromatographs with D) are crystallized from acetone. Appropriate fractions (40–100 L) are concentrated under reduced pressure to a volume of approximately 5 L. The solution (or light slurry) is then transferred to a rotatory evaporater and concentration continued under reduced pressure. Several 1 L portions of acetone are added during the course of the concentration until the methylene chloride is completely displaced. The resulting acetone slurry (approximately 1 L volume) is refrigerated overnight, and the crystals of Marcfortine A are collected and washed with several small portions of cold acetone, and dried under vacuum. Such crystals may be contaminated with several percent of Marcfortine D. Repeated recrystallization from methylene chloride/acetone (displacing methylene chloride as described) affords pure Marcfortine A.

Isolation of marcfortine D

The 4900 L fermentation volume is harvested by passing through a high shear mixer to the harvest vessel. Following transfer, 4% wt./v. of diatomaceous earth and ½ volume of methylene chloride are added. The harvest solution is then filtered using a filter press. The filter cake is washed 2 times with a 10% volume of methylene chloride.

The filtrate obtained is decanted to remove the water (aqueous) phase. The remaining product-rich methylene chloride phase is then concentrated to a volume of 44 L. The concentrate is then polished using a 20% concentrate volume (9 L) of methylene chloride and diatomaceous earth over a filter.

The 53 L polished concentrate is further purified to separate Marcfortine A from other components by silica gel chromatography and crystallization.

Before chromatography, the polished concentrate is divided into four approximately equal aliquots. Each aliquot is chromatographed over a newly packed 9" diameter column prepared from 25 Kg of dry silica gel (bed volume 59 L). The loaded columns are eluted with 120 L of 10% acetone in methylene chloride, 120 L of 20% acetone in methylene chloride, 120 L of 30% acetone in methylene chloride, 160 L of 40% acetone in methylene chloride, and 130 L of acetone collecting the 30 and 40% eluates as 20 L fractions. Eluates are monitored by TLC, using for example a solvent system comprised of 6% isopropanol and 0.3% ammonium hydroxide in methylene chloride to develop Whatman LK6DF silica gel plates. Fractions of Marcfortine A containing marcfortine D are concentrated. One gram of this material is dissolved in formic acid (20 mL, 93%) and standing at 20°–25° for 16 h. After the volatile components are removed with reduced pressure, the residue is subjected to silica gel chromatography (1:20 MeOH:CH$_2$Cl$_2$) to give marcfortine D (100 mg) as a white solid. The structure of the product can be confirmed by NMR spectroscopy and mass spectrometry. HRMS (FAB) M/Z [M+H] calculated for C$_{28}$H$_{35}$N$_3$O$_3$+H: 462.2756; measured: 462.2739.

Procedure 1A

Production and Isolation of Marcfortines A and C. Primary Seed Fermentation Process Seed fermentations are inoculated using agar plugs of isolate Penicillium sp. UC 7780 (NRRL 18887) stored over liquid nitrogen. Three plugs are thawed and used as inoculum for 100 ml of GS-7 seed medium. GS-7 is composed of glucose and cottonseed flour (sold under the trademark "Pharmamedia" by Traders Protein, Procter & Gamble Oilseed Products Co., Memphis, Tenn., U.S.A.) each added at a concentration of 25 g/L of tap water. After formulation, the pH of GS-7 is adjusted to 7.2 using NH$_4$OH. The medium is autoclaved in 100 ml volumes in 500 ml unbaffled fermentation flasks for 30 min. Sterile GS-7 is inoculated as described above and shaken at 250 rpm for 35–58 hr at 23° C.

Production Fermentation Process (shaker flask)

The mature seed cultures are used as inoculum for the production medium at a 1% seed rate. The production medium is composed of glucose 45 g, enzymatically digested casein (sold under the trademark Peptonized Milk Nutrient by Sheffield Products, Norwich, N.Y., U.S.A.) 25 g, yeast extract (sold under the trademark BACTO Yeast Extract Code: 0127 by Difco Laboratories, Detroit, Mich.) 2.5 g per liter of tap water. After formulation, the pH of the production medium is adjusted to 7.0 using potassium hydroxide. This medium is then autoclaved for 30 min in 100 ml volumes contained in 500 ml baffled fermentation flasks. Sterile production medium is inoculated as described above, and shaken for 7–14 days at 250 rpm at 21° C.

Production Fermentation Process (Labraferm tanks)

The mature seed cultures are used as inoculum for the sterile production medium at a 0.5% seed rate. The production medium is described above. After pH adjustment to 7.0 using KOH, 10 L of this medium are autoclaved for 90 min in 12 L Labraferm tanks (New Brunswick Scientific Co., Inc.). The tanks are inoculated at a 0.5% seed rate and stirred at 500 rpm at 20° C. for 5–9 days. The air flow rate is maintained between 10–15 L/min.

Isolation of Marcfortines A and C

Whole fermentation broth (35 l) is macerated at low speed in a large commercial Waring Blender and then blended with an equal volume of methylene chloride. The mixture is stored overnight under refrigeration and then subjected to centrifugation to break the emulsion. The resulting clear methylene chloride layer is drawn off and evaporated under reduced pressure. A concentrated solution of the residue (37.4 g) in methylene chloride is applied to a column of silica gel (1 Kg) slurry packed in methylene chloride. The column is eluted with increasing concentrations of acetone in methylene chloride (10%, 20%, 30%, 40%, and 50% acetone). Fractions are monitored by TLC and appropriate fractions evaporated and crystallized from acetone to give Marcfortine A and Marcfortine C.

Procedure 1B

Production and Isolation of Marcfortines A and C Seed Fermentation Process

Seed fermentations are inoculated using agar plugs of isolate Penicillium sp. UC 7780 (NRRL 18887) stored over liquid nitrogen. Three plugs are thawed and used as inoculum for 100 ml of GS-7 seed medium. GS-7 is composed of glucose and cottonseed flour (sold under the trademark "Pharmamedia" by Traders Protein, Procter & Gamble Oilseed Products Co., Memphis, Tenn., U.S.A.) each added at a concentration of 25 g/L of tap water. After formulation, the pH of GS-7 is adjusted to 7.2 using $NH_4OH$. The medium is autoclaved in 100 ml volumes in 500 ml unbaffled fermentation flasks for 30 min. Sterile GS-7 is inoculated as described above and shaken at 250 rpm for 35–58 hr at 23° C.

Production Fermentation Process (Shake Flask)

The mature seed cultures are used as inoculum for the production medium at a 1% seed rate. The production medium is composed of glucose 20 g, glycerol 15 ml, cottonseed flour (sold under the trademark "Pharmamedia" by Traders Protein, Procter & Gamble Oilseed Products Co., Memphis, Tenn. U.S.A.) 20 g, soybean meal 10 g, and $K_2HPO_4$ 3 g per liter of tap water. After formulation, the pH of the production medium is adjusted to 6.8 using potassium hydroxide. This medium is then autoclaved for 30 min in 100 ml volumes contained in 500 ml baffled fermentation flasks. Sterile production medium is inoculated as described above, and shaken for 7–14 days at 250 rpm at 21° C.

Production Fermentation Process (Labraferm tanks)

The mature seed cultures are used as inoculum for the sterile production medium at a 0.5% seed rate. The production medium is described above. After pH adjustment to 7.0 using KOH, 10 L of this medium are autoclaved for 90 min in 12 L Labraferm tanks (New Brunswick Scientific Co., Inc.). The tanks are inoculated at a 0.5% seed rate and stirred at 500 rpm at 20° C. for 5–9 days. The air flow rate is maintained between 10–15 L/min.

Isolation of Marcfortines A and C

Whole fermentation broth (35 l) is macerated at low speed in a large commercial Waring Blender and then blended with an equal volume of methylene chloride. The mixture is stored overnight under refrigeration and then subjected to centrifugation to break the emulsion. The resulting clear methylene chloride layer is drawn off and evaporated under reduced pressure. A concentrated solution of the residue (37.4 g) in methylene chloride is applied to a column of silica gel (1 Kg) slurry packed in methylene chloride. The column is eluted with increasing concentrations of acetone in methylene chloride (10%, 20%, 30%, 40%, and 50% acetone). Fractions are monitored by TLC and appropriate fractions evaporated and crystallized from acetone to give Marcfortine A and Marcfortine C.

Synthesis of 14-substituted marcfortines

Treatment of marcfortine A (Formula 1a, Chart I) with cyanogen iodide produces a mixture (Formula 5) of 16α-iodo-17β-cyanomarcfortine A and 16β-iodo-17α-cyanomarcfortine A which can be separated by silica gel chromatography. Dehydroiodination of this mixture with potassium hydroxide in methanol leads to 16,17-dehydro-17-cyanomarcfortine A (Formula 6) which is oxidized by selenium dioxide to 17-ketomarcfortine A (Formula 7). Introduction of a double bond between C15 and C16 is accomplished by selenation of position-16 (phenyl selenyl chloride and LDA) followed by oxidation of the selenium intermediate with hydrogen peroxide. Subsequent elimination of the phenylselenic acid gives 15,16-dehydro-17-ketomarcfortine A (Formula 8). This compound is a key intermediate in the synthesis of 14α-hydroxymarcfortine A (Formula 10) to which it can be converted by either of two distinct synthetic routes.

In the first route allylic oxidation of position-14 of this material using potassium bis(trimethylsilyl)amide and 2-phenylsulfonyl-3-phenyloxaziridine is accompanied by oxidation of position-16 to give a mixture of the required 14α-hydroxy-15,16-dehydro-17-ketomarcfortine A (Formula 9a) and 14,15-dehydro-16-hydroxy-17-ketomarcfortine A (Formula 9b). These two products are separated by silica gel chromatography. The compound of Formula 9a is reduced by means of lithium aluminum hydride in THF to 14α-hydroxymarcfortine A (Formula 10), a title compound of this invention disclosure. Alternatively, the compound of Formula 8 (Chart J) is oxidized with selenium dioxide in dioxane to afford a 2:1 mixture of 14α-hydroxy-15,16-dehydro-17-ketomarcfortine A (Formula 9a) and 15,16-dehydro-14,17-diketomarcfortine A (Formula 11). These are separated by means of silica gel chromatography. Each of these compounds is independently converted to 14α-hydroxy-17-ketomarcfortine A (Formula 12a): the compound of Formula 9a by reduction of the 15,16-double bond with lithium triethylborohydride; the compound of Formula 11 by reduction of the carbonyl at position 14 with lithium borohydride. In the latter case, an equal amount of 14β-hydroxy-17-ketomarcfortine A (Formula 12b) is also produced which is removable by chromatography. The compound of formula 12a is reduced with borane tetrahydrofuran (THF) complex to give 14α-hydroxymarcfortine A (Formula 10).

14α-Hydroxy-15,16-dehydro-17-ketomarcfortine A (Formula 9a, Chart K) is reduced with lithium triethylborohydride to 14α-hydroxy-17-ketomarcfortine A (Formula 12a). This is transformed by means of a Swern oxidation using oxalyl chloride and DMSO to 14,17-diketomarcfortine A (Formula 13). Treatment with methylmagnesium bromide in a Grignard reaction produces a mixture of 14α-hydroxy-14β-methyl-17-ketomarcfortine A (Formula 14a) and 14β-hydroxy-14α-methyl-17-ketomarcfortine A (Formula 14b) which are separated by silica gel chromatography. The ratio of the products is dependent upon the solvent used: methylene chloride gives a 6:1 ratio, while THF gives a >50:1 ratio, respectively. Reduction of the compound of Formula 13a with lithium aluminum hydride gives 14α-hydroxy-14β-methylmarcfortine A (Formula 15).

Swern oxidation of 14α-hydroxymarcfortine A (Formula 10, Chart L) provides 14-ketomarcfortine A (Formula 16), which is reduced with sodium borohydride to 14-β-hydroxymarcfortine A (Formula 17). Treatment of 14-ketomarcfortine A (Formula 16) with ethylmagnesium bromide in a grignard reaction produces 14α-hydroxy-14-ethylmarcfortine A (Formula 19). Treatment of 14α-hydroxymarcfortine A (Formula 10) with m-chloroperoxybenzoic acid produces 14α-hydroxymarcfortine A N-oxide (Formula 18). 14β-methylmarcfortine A can be prepared from 14α-hydroxy-14β-methylmarcfortine A by means of dehydroxylation. Thus, 14α-hydroxy-14β-methylmarcfortine A is treated with phenylchlorothionoformate in the presence of base. This thionoformate derivative of 14α-hydroxy-14β-methylmarcfortine A is reduced with tri-n-butyltin hydride to produce 14β-methylmarcfortine A.

Alternatively, 14α-hydroxymarcfortine A can be synthesized from marcfortine A (Chart M). Treatment of marcfortine A with sodium bicarbonate and iodine in aqueous tetrahydrofuran produces 17-ketomarcfortine A (Formula 7), which can be disulfenylated by using LDA and phenyl disulfide to give 16-dithiophenyl-17-keto marcfortine A (Formula 20, CHART M) in 60% yield from marcfortine A. Oxidation with m-chloroperoxybenzoic acid produces 16-thiophenyl-16-sulfoxyphenyl-17-ketomarcfortine A (Formula 21), which eliminates in refluxing toluene to yield 15,16-dehyro-16-thiophenyl-17-ketomarcfortine A (Formula 22). Subsequent treatment with m-chloroperoxybenzoic acid produces 15,16-dehydro-16-sufoxyphenyl-17-ketomarcfortine A (Formula 23), which undergoes rearrangement by using diethyl amine in methanol to produce 15,16-dehydo-14α-hydroxy-17-ketomarcfortine A (Formula 9a).

14α-Hydroxy-15α-methylmarcfortine A (Formula 35, Chart N) can be synthesized from 15,16-dehydro-14α-hydroxy-17-ketomarcfortine A (Formula 9a, Chart N). Thus, 15,16-dehydro-14α-hydroxy-17-ketomarcfortine A (Formula 9a) is treated with either methylmagnesium bromide or lithium dimethylcopper to produce 15α-methyl-14α-hydroxy-17-ketomarcfortine A (Formula 34), which is reduced with borane-dimethylsulfide complex to produce 15α-methyl-14α-hydroxymarcfortine A (Formula 35). 15α-Methyl-14α-hydroxy-17-ketomarcfortine A (Formula 34) is transformed by means of a Swern Oxidation using oxalyl chloride and DMSO to 15α-methyl-14,17-diketomarcfortine A (Formula 36). Treatment with methylmagnesium bromide in a Grignard reaction produces 15α-Methyl-14α-hydroxy-14β-methyl-17-ketomarcfortine A (Formula 37), which is reduced with borane-dimethylsulfide complex to produce 15α-methyl-14α-hydroxy-14β-methylmarcfortine A (Formula 38).

These previously described procedures can be used to produce 14-substituted marcfortine B, C and D derivatives.

PREPARATION 1

16-Iodo-17-cyanomarcfortine A as a mixture of diastereomers (Formula 5)

Solid cyanogen iodide (11.7 g, 76.5 mmol) is added to a solution of marcfortine A (10.5 g, 22 mmol) in $CHCl_3$ (150 mL) and the reaction mixture heated under reflux until all of the marcfortine A has been consumed (about 5 h). The resulting black solution is cooled to 20°–25°, diluted with $CH_2Cl_2$ (100 mL), washed with sat $NaHCO_3$, and then washed with a solution of $Na_2SO_3$. The organic phase is separated, dried over $MgSO_4$, and concentrated to dryness. The resulting crude solid is subjected to silica gel chromatography (3:2-EtOAc:hexane) to give 16-Iodo-17-cyanomarcfortine A (12.5 g, 90%) as a white powdery solid. The structure of the product can be confirmed by nuclear magnetic resonance spectroscopy and mass spectrometry.

PREPARATION 2

16,17-Dehydro-17-cyanomarcfortine A (Formula 6)

16-Iodo-17-cyanomarcfortine A (9.5 g, 15 mmol) is dissolved in MeOH (150 mL), and aqueous KOH (45%, 3 mL) is added. The reaction mixture is stirred at 20°–25° for 2 h. Water is added and the resulting white precipitate collected by filtration, washed with water, and dried overnight under vacuum to give 16,17-Dehydro-17-cyanomarcfortine A (6.6 g, 75%) as a white powder. The structure of the product can be confirmed by nuclear magnetic resonance spectroscopy and mass spectrometry.

MS (FAB) M/Z [M+H]: 501.

PREPARATION 3

17-Ketomarcfortine A (Formula 7)

Selenium dioxide (2.9 g, 26 mmol) is added to a solution of 16,17-Dehydro-17-cyanomarcfortine A (6.0 g, 10 mmol) in 95% EtOH (100 mL) and the reaction mixture stirred at 20°–25° for 2 h. The reaction is quenched by adding sat $NaHCO_3$ (100 mL). The resulting mixture is extracted with $CH_2Cl_2$ (2×200 mL). The extracts are combined, dried ($MgSO_4$), and concentrated to give 7 g of crude product. This material is purified by silica gel chromatography (EtOAc) to give 17-ketomarcfortine A (3.6 g, 75%) as a white solid. The structure of the product can be confirmed by nuclear magnetic resonance spectroscopy and mass spectrometry.

HRMS (FAB) M/Z [M+H] calculated for $C_{28}H_{33}N_3O_5$+H: 492.2498; measured: 492.2478.

Alternatively, and more preferably, the title compound can be synthesized by using p-toluenesufonic acid. Thus, p-toluenesulfonic acid monohydrate (1 g) is to a solution of 16,17-dehydro-17-cyanomarcfortine A (10 g) in 95% MeOH (50 mL) and the reaction mixture stirred at 20°–25° for 1 h. Triethyl amine (2 mL) is added to the mixture and the solvent was evaporated. The residue is triturated with 10% aqueous sodium carbonate solution (100 mL) and the solid is filter and dried to give the title compound as a solid (90% yield). The structure of the product can be confirmed by nuclear magnetic resonance spectroscopy and mass spectrometry.

PREPARATION 4

15,16-Dehydro-17-ketomarcfortine A (Formula 8)

A solution of lithium diisopropylamide is prepared from a solution of n-butyl lithium (1.6M, 9.9 mL, 15.4 mmol) in hexane and diisopropylamine (2.2 mL, 15.7 mmol). This is diluted with anhydrous tetrahydrofuran (THF, 20 mL) and cooled to at –78°. A solution of 17-ketomarcfortine A (2.0 g, 4.1 mmol) in anhydrous THF (20 mL) is added dropwise and the reaction mixture allowed to warm to –40° during 1 h. The mixture is again cooled to –78° and treated dropwise with phenyl selenium chloride (19 mg, 5.2 mmol) in THF (10 mL). After 5 min the reaction is quenched with sat $NaHCO_3$, extracted with $CH_2Cl_2$, dried ($MgSO_4$), and concentrated to give a yellow solid which can be used without further purification. This material is dissolved in THF (150 mL) and treated with $H_2O_2$ (30%, 1.5 mL) at 0°. The cooling bath is removed and the reaction mixture stirred for 30 min at 20°–25°. The reaction is quenched by adding NaOH (1N, 100 mL). The mixture is extracted with $CH_2Cl_2$ (2×200 mL). The extracts are combined, dried ($MgSO_4$), and concentrated to give crude product. This material is purified by silica gel chromatography (EtOAc) to give 15,16-dehydro-17-ketomarcfortine A (1.3 g,65%) as a white solid. The structure of the product is confirmed by nuclear magnetic resonance spectroscopy and mass spectrometry. HRMS (FAB) M/Z [M+H] calculated for $C_{28}H_{31}N_3O_5$+H: 490.2342; measured: 490.2345.

PREPARATION 5

14α-Hydroxy-15,16-dehydro-17-ketomarcfortine A (Formula 9a) Using Oxaziridine Chemistry A solution of potassium bis(trimethylsilyl)amide in toluene (0.5M, 1 mL, 0.5 mmol) is added dropwise to a solution of 15,16-dehydro-17-ketomarcfortine A (66 mg, 0.14 mmol) in THF (2 mL) at –78°. The resulting pale yellow, turbid solution is allowed to warm to –40° during 1 h. The reaction mixture is cooled –78°, stirred 15 min, and then treated by the dropwise addition of a solution of 2-phenylsulfonyl-3-phenyloxaziridine (42 mg, 0.16 mmol) in THF (2 mL). The mixture is stirred 5 min after which the reaction is quenched by adding NaHCO$_3$. The mixture is extracted with CH$_2$Cl$_2$ (2×25 mL). The extracts are combined, dried (MgSO$_4$), and concentrated to give crude material. This is purified by preparative thin layer chromatography (silica gel, EtOAc) to give 14α-Hydroxy-15,16-dehydro-17-ketomarcfortine A (8 mg, 12%) as a white solid. The structure can be confirmed by nuclear magnetic resonance spectroscopy and mass spectrometry. HRMS (FAB) M/Z [M+H] calculated for C$_{28}$H$_{31}$N$_3$O$_6$+H: 506.2291; measured: 506.2280. 14,15-Dehydro-16-hydroxy-17-ketomarcfortine A (14 mg, 20%) is also obtained from the layer. Its structure can be confirmed by nuclear magnetic resonance spectroscopy.

PREPARATION 6

14α-Hydroxy-15,16-dehydro-17-ketomarcfortine A (Formula 9a), 15,16-dehydro-14,17-diketomarcfortine A (Formula 11) and 14,15-dehydro-16,17-diketomarcfortine A (Formula 24) Using Selenium Dioxide 15,16-Dehydro-17-ketomarcfortine A (1.29 g, 2.6 mmol) is dissolved in p-dioxane (30 mL) and treated with selenium dioxide (390 mg). The mixture is refluxed for 1 h and the solvent evaporated in vacuo. The residue is triturated with methylene chloride (30 mL) and filtered. The filtrate is concentrated, and the residue subjected to silica gel chromatography (1:20 MeOH:EtOAc) to give 14α-hydroxy-15,16-dehydro-17-ketomarcfortine A (430 mg, 32%) as a solid. 15,16-Dehydro-14,17-diketomarcfortine A (Formula 11, 212 mg, 16%) is also obtained from the chromatography. 14,15-Dehydro-16,17-diketomarcfortine A (Formula 24, 106 mg, 8%) is also obtained from the chromatography. The structure of these products can be confirmed by nuclear magnetic resonance spectroscopy and mass spectrometry.

PREPARATION 7

15,16-dehydro-14,17-diketomarcfortine A (Formula 11)

14α-Hydroxy-15,16-dehydro-17-ketomarcfortine A (60 mg, Formula 9a) is dissolved in methylene chloride (10 mL) and treated with manganese dioxide (60 mg). The mixture is stirred at 20°–25° for 1 h and concentrated. Preparative thin layer chromatography of the residue on silica gel (50% methylene chloride in EtOAc) afforded 15,16-dehydro-14,17-diketomarcfortine A (Formula 11, 35 mg, 60%). The structure of these products can be confirmed by nuclear magnetic resonance spectroscopy and mass spectrometry.

PREPARATION 8

14α-hydroxymarcfortine A (Formula 10)

14α-Hydroxy-15,16-dehydro-17-ketomarcfortine A (20 mg, 0.040 mmol) is dissolved in THF (5 mL) and treated with a solution of lithium aluminum hydride (1M, 0.11 mL, 0.11 mmol) in THF at 0°. The mixture is stirred for 0.5 h at 0° after which a solution of NaHCO$_3$ (10%) is added. The mixture is extracted with CH$_2$Cl$_2$ (2×10 mL). The extracts are combined, dried (MgSO$_4$), and the solvent removed under reduced pressure. Preparative thin layer chromatography of the residue on silica gel (10% MeOH in EtOAc) gives the title compound, HRMS (FAB, M/Z) [M+H] calculated for C$_{28}$H$_{35}$N$_3$O$_5$+H=494.2655, measured=494.2653.

PREPARATION 9

14α-Hydroxy-17-ketomarcfortine A (Formula 12a)

14α-Hydroxy-15,16-dehydro-17-ketomarcfortine A (formula 9a, 50 mg, 0.1 mmol) is dissolved in THF (5 mL) and treated with a solution of lithium triethylborohydride in THF (1M, 0.7 mL) at −78°. The mixture is stirred for 0.5 h at −78°. The reaction is quenched by adding MeOH (1 mL), and the mixture is concentrated. The resulting solid is subjected to silica gel chromatography (1:20 MeOH:CH$_2$Cl$_2$) to give 14α-hydroxy-17-keto marcfortine A (43 mg, 86%) as a white solid. The structure of the product can be confirmed by NMR spectroscopy and mass spectrometry. HRMS (FAB) M/Z [M+H] calculated for C$_{28}$H$_{33}$N$_3$O$_6$+H: 508.2447; measured: 508.2437.

PREPARATION 10

Preparation of 14α-hydroxy-17-ketomarcfortine A (Formula 12a) from 15,16-dehydro-14,17-diketomarcfortine A (Formula 11)

15,16-Dehydro-14,17-diketomarcfortine A (470 mg, 0.93 mmol) is dissolved in THF and treated with a solution of lithium borohydride in THF (1M, 2 mL) at room temperature. The mixture is stirred for 2 h after which a solution of NaHCO$_3$ (10%) is added. The mixture is extracted with CH$_2$Cl$_2$ (2×20 mL). The extracts are combined, dried (MgSO$_4$), and the solvent evaporated. The residue contains a mixture of the two epimers which are readily separated by silica gel chromatography (1:20 MeOH:EtOAc): 14α-hydroxy-17-ketomarcfortine A (90 mg, 19%) and 14β-hydroxy-17-ketomarcfortine A (94 mg, 20%). The structure of both products can be confirmed by NMR spectroscopy and mass spectrometry.

PREPARATION 11

Preparation of 14α-hydroxymarcfortine A (Formula 10) from 14α-hydroxy-17-ketomarcfortine A (Formula 12a)

14α-Hydroxy-17-ketomarcfortine A (413 mg, 0.81 mmol) is dissolved in THF (20 mL) and treated with a solution of borane THF complex in THF (1M, 2.43 mL) at 0°. The mixture is stirred for 2.25 h. The mixture is stirred for 0.5 h after which MeOH (3 mL) is added. After the solvent is evaporated, the residue is subjected to silica gel chromatography (1:16 MeOH:EtOAc) to give 14α-hydroxymarcfortine A (250 mg, 92% yield based on starting material recovered) and 14α-hydroxy-17-ketomarcfortine A (starting material, 140 mg, 34%).

PREPARATION 12

14,17-Diketomarcfortine A (Formula 13)

A solution of oxalyl chloride (40 μL) in anhydrous CH$_2$Cl$_2$ (5 mL) is treated with dimethyl sulfoxide (45 μL) at −78°. The mixture is stirred for 1 h at −78°. A solution of 14α-hydroxy-17-ketomarcfortine A (27 mg) in CH$_2$Cl$_2$ (2 mL) is added dropwise. The reaction mixture is stirred 20 min at −78°. Triethylamine (0.3 mL) is added to the reaction mixture which is allowed to warm to room temperature during 20 min. The mixture is partitioned between 10% Na$_2$CO$_3$ (10 mL) and CH$_2$Cl$_2$ (10 mL). The organic layer is dried (MgSO$_4$) and concentrated. The residue is subjected to silica gel chromatography (1:20 MeOH:CH$_2$Cl$_2$) to give 14,17-Diketomarcfortine A (22 mg, 80%) as a white solid. The structure of the product can be confirmed by NMR spectroscopy and mass spectrometry. HRMS (FAB) M/Z [M+H] calculated for C$_{28}$H$_{31}$N$_3$O$_6$+H: 506.2291; measured: 506.2280.

PREPARATION 13

14α-Hydroxy-14β-methyl-17-ketomarcfortine A (Formula 14a)

A solution of 14,17-Diketomarcfortine A (16 mg, 0.032 mmol) in CH$_2$Cl$_2$ (5 mL) at −78° is treated with a solution of methylmagnesium bromide (3M, 0.16 mL, 0.48 mmol) in Et$_2$O at −78°. The resulting mixture is stirred for 0.5 h at −78°. The reaction is quenched by adding 10% Na$_2$CO$_3$ (a few drops). The mixture was diluted with CH$_2$Cl$_2$ (10 mL), dried (MgSO$_4$), and concentrated. The residue is subjected to silica gel chromatography (1:20 MeOH:CH$_2$Cl$_2$) to give 14α-hydroxy-14β-methyl-17-ketomarcfortine A (8 mg, 50%, R$_f$=0.25) as a white solid. The structure of the product can be confirmed by NMR spectroscopy and mass spectrometry. HRMS (FAB) M/Z [M+H] calculated for C$_{29}$H$_{35}$N$_3$O$_6$+H: 522.2604; measured: 522.2620. Also obtained from the layer is 14β-hydroxy-14α-methyl-17-ketomarcfortine A (1.2 mg, 7%, R$_f$=0.4) as a white solid. The structure of the product can be confirmed by NMR spectroscopy and mass spectrometry. HRMS (FAB) M/Z [M+H] calculated for C$_{29}$H$_{35}$N$_3$O$_6$+H: 522.2604; measured: 522.2630. The 6:1 ratio of products thus obtained is increased to greater than 50:1 and the yield increased to 80% when THF is used as the reaction solvent in place of CH$_2$Cl$_2$.

PREPARATION 14

14α-hydroxy-14β-methylmarcfortine A (Formula 15)

A solution of 14α-hydroxy-14β-methyl-17-ketomarcfortine A (5 mg, 0.01 mmol) in THF (5 mL) is treated with a solution of Lithium Aluminum Hydride (1M, 0.03 mL, 0.03 mmol) in THF at 0°. The mixture is stirred for 0.5 h at 0° after which a solution of NaHCO$_3$ (10%) is added. The mixture is extracted with CH$_2$Cl$_2$ (2×5 mL). The extracts are combined, dried (MgSO$_4$), and the solvent evaporated. Preparative thin layer chromatography of the residue on silica gel (1:20 MeOH:CH$_2$Cl$_2$) afforded 14α-hydroxy-14β-methylmarcfortine A (2 mg, 40%). The structure of the product can be confirmed by NMR spectroscopy and mass spectrometry. HRMS (FAB) M/Z [M+H] calculated for C$_{29}$H$_{37}$N$_3$O$_5$+H: 508.2811; measured: 508.2816.

PREPARATION 15

14-Ketomarcfortine A (Formula 16)

A solution of oxalyl chloride (150 μL) in anhydrous CH$_2$Cl$_2$ (20 mL) is treated with DMSO (170 μL) at −78°. The mixture is stirred for 1 h at −78°. A solution of 14α-hydroxymarcfortine A (110 mg) in CH$_2$Cl$_2$ (5 mL) is added dropwise. The reaction mixture is stirred 20 min at −78°. Triethylamine (1 mL) is added to the reaction mixture which is allowed to warm to room temperature during 20 min. The mixture is partitioned between 10% Na$_2$CO$_3$ (20 mL) and CH$_2$Cl$_2$ (20 mL). The organic layer is dried (MgSO$_4$) and concentrated. The residue is subjected to silica gel chromatography (1:25 MeOH:CH$_2$Cl$_2$) to give 14-ketomarcfortine A (82 mg, 75%) as a white solid. The structure of the product can be confirmed by NMR spectroscopy and mass spectrometry. HRMS (FAB) M/Z [M+H] calculated for C$_{28}$H$_{33}$N$_3$O$_5$+H: 492.2498; measured: 492.2510.

PREPARATION 16

14β-Hydroxymarcfortine A (Formula 17)

A solution of 14-ketomarcfortine A (10 mg) in MeOH (2 mL) is treated with sodium borohydride (5 mg) at 0°. The mixture is stirred for 0.5 h at 0° after which a solution of NaHCO$_3$ (10%) is added. The mixture is extracted with CH$_2$Cl$_2$ (2×10 mL). The extracts are combined, dried (MgSO$_4$), and the solvent evaporated. Preparative thin layer chromatography of the residue on silica gel (1:16 MeOH:EtOAc) affords 14β-hydroxymarcfortine A (5 mg, 50%). The structure of the product can be confirmed by NMR spectroscopy and mass spectrometry. HRMS (FAB) M/Z [M+H] calculated for C$_{28}$H$_{35}$N$_3$O$_5$+H: 494.2655; measured: 494.2653.

PREPARATION 17

14α-Hydroxymarcfortine A N-oxide (Formula 18)

A solution of 14α-hydroxymarcfortine A (15 mg) in CH$_2$Cl$_2$ (3 mL) is treated with m-chloroperoxybenzoic acid (15 mg) at 0°. After the mixture is stirred for 0.5 h at 0°, treated with triethyl amine (30 μL) and concentrated. Preparative thin layer chromatography of the residue on silica gel (1:8 MeOH:CH$_2$Cl$_2$) affords 14α-hydroxymarcfortine A N-oxide (12 mg, 80%). The structure of the product can be confirmed by mass spectrometry. HRMS (FAB) M/Z [M+H] calculated for C$_{28}$H$_{35}$N$_3$O$_6$+H: 510.2604; measured: 510.2615.

PREPARATION 18

14α-Hydroxy-14β-ethylmarcfortine A (Formula 19)

A solution of 14-ketomarcfortine A (25 mg, 0.05 mmol) in THF (5 mL) at −78° is treated with a solution of ethylmagnesium bromide (3M, 0.15 mL, 0.45 mmol) in Et$_2$O at −78°. The resulting mixture is stirred for 0.5 h at −78°. The reaction mixture is allowed to warm to room temperature during 20 min. The reaction is quenched by adding 10% Na$_2$CO$_3$ (a few drops). The mixture was diluted with CH$_2$Cl$_2$ (10 mL), dried (MgSO$_4$), and concentrated. The residue is subjected to silica gel chromatography (1:20 MeOH:CH$_2$Cl$_2$) to give 14α-hydroxy-14β-ethylmarcfortine A (10 mg, 45%) as a white solid. The structure of the product can be confirmed by NMR spectroscopy and mass spectrometry. HRMS (FAB) M/Z [M+H] calculated for C$_{30}$H$_{39}$N$_3$O$_5$+H: 522.2968; measured: 522.2983.

PREPARATION 19

Preparation of 14β-methylmarcfortine A from 14α-hydroxy-14β-methylmarcfortine A

A solution of potassium bis(trimethylsilyl)amide in toluene (0.5M, 1 mL, 0.5 mmol) is added dropwise to a solution of 14α-hydroxy-14β-methylmarcfortine A (66 mg, 0.14 mmol) in THF (2 mL) at −78°. The resulting pale yellow, turbid solution is allowed to warm to −40° during 1 h. The reaction mixture is cooled −78°, stirred 15 min, and then treated by the dropwise addition of a solution of phenylchlorothionoformate (0.094 mL, 0.7 mmol) in THF (2 mL). After 10 min the dry ice bath is removed. After further reaction for 3 h, the reaction is quenched by adding NaHCO$_3$. The mixture is extracted with CH$_2$Cl$_2$ (2×25 mL). The extracts are combined, dried (MgSO$_4$), and concentrated to give crude material. This is purified by preparative thin layer chromatography (silica gel, EtOAc) to give 14α-O-phenoxythiocarbonyl-14β-methylmarcfortine A.

To a solution of 14α-O-phenoxythiocarbonyl-14β-methylmarcfortine A (64 mg, 0.1 mmol) in toluene (5 mL) is added AIBN (3.3 mg) followed by addition of tributyltin hydride (54 μL, 0.2 mmol). The mixture is refluxed for 3 h. After the solvent is evaporated, the residue is purified by preparative thin layer chromatography (silica gel, EtOAc) to give 14β-methylmarcfortine A. The structure can be confirmed by nuclear magnetic resonance spectroscopy and mass spectrometry.

PREPARATION 20

An Alternative Synthesis of 17-ketomarcfortine A (Formula 7)

To marcfortine A (65 g, 0.136 mol) and sodium bicarbonate (137 g, 1.63 mol) in tetrahydrofuran (THF, 2 L) and water (1.25 L) at reflux is added iodine (206 g, 0.81 mol) dropwise in THF (1.25 l) over a one hour period. (Alternatively, the mixture can be stirred at room temperature for 16 hours.) After being allowed to slowly cool to ambient temperature (2.5 h), the reaction is quenched with saturated sodium thiosulfate ($Na_2S_2O_3$, 1.5 L) and extracted with ethyl acetate (2×1 L). The combined organic layers are washed with saturated sodium thiosulfate (1 L), dried ($MgSO_4$), filtered, evaporated and dried overnight in the vacuum oven (65° C.) to give 62 g of crude 17-ketomarcfortine A (Formula 7) as a yellow solid. $^1H$ NMR (300 MHz, $CDCl_3$): δ7.68 (s, 1H), 6.80 (d, 1H), 6.70 (d, 1H), 6.32 (d, 1H), 4.90 (d, 1H), 3.75 (q, 2H), 3.23 (t, 1H), 3.09 (s, 3H), 2.80 (d, 1H), 2.65 (d, 1H), 2.49–2.21(m, 2H), 2.08 (d, 1H), 1.98–1.45 (m, 5H), 1.46 (s, 3H), 1.44 (s, 3H), 1.09 (s, 3H), 0.90 (s, 3H).

Alternatively, ICl can be used instead of iodine.

PREPARATION 21
16-Dithiophenyl-17-ketomarcfortine A (Formula 20)

The crude 17-ketomarcfortine A (5 g, 10.2 mmol) is added via a cannula in THF (150 mL) at −78° C. to an LDA solution which was prepared by adding n-BuLi (1.6M, 24.8 mL, 0.04 mol) dropwise to diisopropyl amine (5.7 mL, 0.041 mol) at 0° C. in THF (100 mL). The reaction mixture is allowed to slowly warm to −50° C. over one hour. The resulting turbid red-brown mixture is then treated with phenyl disulfide (4.4 g, 0.02 mol). The reaction is immediately quenched with saturated sodium bicarbonate solution (100 mL) and extracted with methylene chloride ($CH_2Cl_2$, 300 mL). The organic phase was dried ($MgSO_4$), concentrated (8 g), and chromatographed on silica gel (120 g, 60% ethyl acetate/hexane as eluant) to yield the the title compound as an off white solid (4.4 g, 61% from marcfortine A). FAB-MS 708 ($M^++H$); $^1H$ NMR (300 MHz, $CDCl_3$) δ7.74 (s, 1H), 7.71 (d, 2H), 7.64 (d, 2H), 7.45–7.30 (m, 6H), 6.81 (d, 1H), 6.72 (d, 1H), 6.32 (d, 1H), 4.91 (d, 1H), 3.70 (q, 2H), 3.16 (t, 1H), 3.01 (s, 3H), 2.75 (d, 1H), 2.53 (dt, 1H), 2.35 (dt, 1H), 2.15–1.50 (m, 5H), 1.47 (s, 3H), 1.45 (s, 3H), 1.06 (s, 3H), 0.82 (s, 3H).

PREPARATION 22
16-Thiophenyl-16-sulfoxyphenyl-17-ketomarcfortine A (Formula 21)

To 16-dithiophenyl-17-ketomarcfortine A (10 g, 14 mmol) in $CH_2Cl_2$ (250 mL) at −78° C. under a nitrogen atmosphere is added m-chloroperoxybenzoic acid (m-CPBA, 64%, 4.2 g, 15.5 mmol) dropwise in $CH_2Cl_2$ (200 mL) for 15 minutes. The reaction is immediately quenched with saturated sodium thiosulfate (200 mL), diluted with saturated $NaHCO_3$ (200 mL), and extracted into $CH_2Cl_2$ (200 mL). Drying ($MgSO_4$), followed by concentration under reduced pressure gives of 11 g of crude 16-thiophenyl-16-sulfoxyphenyl-17-ketomarcfortine A (Formula 21). $^1H$ NMR (300 MHz, $CDCl_3$) δ8.0–7.29 (m, 11H), 6.80 (d, 1H), 6.70 (d, 1H), 6.31 (d, 1H), 4.90 (d, 1H) 3.68 (d, 1H), 3.41 (d, 1H), 3.14 (t, 1H), 3.07 (s, 3H), 2.82 (dt, 1H), 2.80–2.65 (m, 2H), 2.16 (dt, 1H), 2.05–1.1 (m, 4H), 1.47 (s, 3H), 1.43 (s, 3H), 0.96 (s, 3H), 0.83 (s, 3H).

PREPARATION 23
16-Thiophenyl-15,16-dehydro-17-ketomarcfortine A (Formula 22)

The crude 16-thiophenyl-16-sulfoxyphenyl-17-ketomarcfortine A (Formula 21, 11 g) is refluxed in toluene (250 mL) for 45 minutes, cooled to room temperature, diluted with saturated sodium bicarbonate (300 mL) and extracted with EtOAc (300 mL). The organic layer is dried ($MgSO_4$) and concentrated to give 10.6 g of crude 16-thiophenyl-15,16-dehydro-17-ketomarcfortine A (Formula 22). FAB-MS 598($M^++H$); HRMS M/Z ($M^++H$, $C_{34}H_{35}N_3O_5S+H_1$), calc. 598.2376, obsd. 598.2387. $^1H$ NMR (300 MHz, $CDCl_3$) 8.18 (s, 1H), 7.55–7.45 (m, 2H), 7.29–7.45 (m, 3H), 6.83 (d, 1H), 6.70 (d, 1H), 6.34 (d, 1H), 5.92 (dt, 1H), 4.91 (d, 1H), 3.87 (q, 2H), 3.30 (dd, 1H), 3.21 (t, 1H), 3.08 (s, 3H), 2.80 (d, 1H), 2.35 (dd, 1H), 2.10 (d, 1H), 2.03 (dd, 1H), 1.78 (dd, 1H), 1.46 (s, 3H), 1.44 (s, 3H), 1.11 (s, 3H), 0.88 (s, 3H).

PREPARATION 24
16-Sulfoxyphenyl-15,16-dehydro-17-ketomarcfortine A (Formula 23)

To the crude 16-thiophenyl-15,16-dehydro-17-ketomarcfortine A (Formula 22, 10.6 g) in methylene chloride (300 mL) at −78° C. is added m-CPBA (64%, 2.8 g) dropwise in $CH_2Cl_2$ (125 mL). The reaction is quenched with saturated sodium thiosulfate (300 mL) and saturated sodium bicarbonate (300 mL), then extracted into methylene chloride (300 mL). The organic layer is dried ($MgSO_4$), filtered and concentrated to give 13 g of crude 16-sulfoxyphenyl-15,16-dehydro-17-ketomarcfortine A (Formula 23). $^1H$ NMR (300 MHz, $CDCl_3$) 7.75–7.3 (m, 5H), 6.81 (s, 1H), 6.75–6.6 (m, 2H), 6.31 (d, 1H), 4.90 (d, 1H), 3.78–3.58 (m, 2H), 3.22 (t, 1H), 2.98 (s, 3H), 2.88–2.45 (m, 2H), 2.12–1.55 (m, 5H), 1.46 (s, 3H), 1.44 (s, 3H), 1.12 (s, 3H), (s, 3H), 0.88 (s, 3H).

PREPARATION 25
14α-Hydroxy-15,16-dehydro-17-ketomarcfortine A (Formula 9a)

To the crude 16-sulfoxyphenyl-15,16-dehydro-17-ketomarcfortine A (Formula 23, 13 g) in aqueous MeOH (10/1, 300 mL) is added diethyl amine (15 mL). After refluxing for 0.5 h the reaction mixture is cooled to room temperature, diluted with water (450 mL), and extracted into $CH_2Cl_2$ (500 mL). Drying ($MgSO_4$), followed by concentration and silica gel chromatography (130 g, 30% acetone/$CH_2Cl_2$ as eluant) produces 14α-hydroxy-15,16-dehydro-17-marcfortine A (Formula 9a, 3.6 g, 50% yield from 16-dithiophenyl-17-keto marcfortine A) as a white solid.

PREPARATION 26
14α-Hydroxy-14β-vinylmarcfortine A (Formula 30)

A solution of 14-ketomarcfortine A (200 mg, 0.4 mmol) in THF (5 mL) at −78° is treated with a solution of vinylmagnesium bromide (1M, 4.0 mL, 4 mmol) in THF at −78°. The resulting mixture is stirred for 2 h at −78° and warmed to room temperature. It is stirred at room temperature for 2 h. The reaction is quenched by adding 10% $Na_2CO_3$ (3 mL). The mixture was diluted with $CH_2Cl_2$ (30 mL), washed with saturated ammonium chloride solution, dried ($MgSO_4$), and concentrated. The residue is subjected to silica gel chromatography (6:4 hexane:acetone) to give 14α-hydroxy-14β-vinylmarcfortine A (120 mg, 60%, $R_f$=0.45) as a white solid. $^1H$ NMR (300 MHz, $CDCl_3$) δ7.86 (s, NH), 6.78 & 6.67 (d, J=8.1 Hz, $C_4$—H & $C_5$—H), 6.32 (d, J=7.7 Hz, $C_{24}$—H), 6.58 (dd, J=17.4, 10.9 Hz, 1H, vinyl), 5.43 (d, J=17.4 Hz, 1H, vinyl), 5.18 (d, J=10.9 Hz, 1H, vinyl), 4.89 (d, J=7.7 Hz, $C_{25}$—H), 3.7 (br, 1H) 3.11 (s, 3H, N—Me), 2.95 (t, 1H, $C_{20}$—H), 2.8–1.5 (m, 12H), 1.44 (s, 6H, $C_{27}$—H & $C_{28}$—H), 1.08 (s, 3H), 0.82 (s, 3H). MS (FAB) M/Z [M+H]: 520

PREPARATION 27
14α-Hydroxy-14β-methylmarcfortine A N-oxide (Formula 32)

A solution of 14α-hydroxymarcfortine A (30 mg) in $CH_2Cl_2$ (3 mL) is treated with m-chloroperoxybenzoic acid (20 mg) at 0°. After the mixture is stirred for 0.5 h, then partitioned between 5% aqueous sodium bicarbonate (10 mL) and methylene chloride (20 mL). The layers are separated and the aqueous layer extracted with methylene chloride (10 mL). The combined extracts are dried with magnesium sulfate, filtered, and evaporated under vacuum at 0°, treated with triethyl amine (30 µL) and concentrated to produce the title compound as a solid (20 mg). $^1$H NMR (300 MHz, CD$_3$OD) δ6.91 & 6.70 (d, J=8.1 Hz, C$_4$—H & C$_5$—H), 6.36 (d, J=7.7 Hz, C$_{24}$—H), 4.91 (d, J=7.7 Hz, C$_{25}$—H), 4.08 & 3.76 (AB q, J=12.9 Hz, 2H, C$_{12}$—H), 3.5–3.1 (m, 4H), 3.12 (s, 3H, N-Me), 2.8–1.6 (m, 7H), 1.46 & 1.44 (2s, 6H, C$_{27}$—H & C$_{28}$—H), 1.50 (s, 3H, C$_{14}$-Me), 1.20 (s, 3H), 0.93 (s, 3H).

PREPARATION 28

14α-Hydroxy-15α-methylmarcfortine A (Formula 35)

14α-Hydroxy-15α-methyl-17-ketomarcfortine A (90 mg, 0.18 mmol) is dissolved in THF (10 mL) and treated with borane dimethyl sulfide complex (12M, 0.18 mL) at 0°. The mixture is stirred for 2 h at 0°, then MeOH (0.4 mL) is added and stirred for an additional 1 h. After the solvent is evaporated, the residue is subjected to silica gel chromatography (30:70 acetone:methylene chloride) to give 14α-hydroxy-15α-methylmarcfortine A (20 mg) as a solid. $^1$H NMR (300 MHz, CDCl$_3$) δ8.39 (s, NH), 6.79 & 6.70 (d, J=8.1 Hz, C$_4$—H & C$_5$—H), 6.36 (d, J=7.7 Hz, C$_{24}$—H), 4.91 (d, J=7.7 Hz, C$_{25}$—H), 3.81 (br, 1H, C$_{14}$—H), 3.67 (d, 1H, J=11.7 Hz, C$_{12}$—H), 3.03 (t, 1H, C$_{20}$—H), 3.11 (s, 3H, N-Me), 2.68 & 1.86 (d, 2H, J=15.7 Hz, C$_{10}$—H), 2.7–1.2 (m, 8H), 1.44 (2s, 6H, C$_{27}$—H & C$_{28}$—H), 1.02 (d, 3H, J=6.8 Hz, C$_{15}$-Me), 1.11 (s, 3H), 0.85 (s, 3H). HRMS (FAB) M/Z [M+H] calculated for C$_{29}$H$_{37}$N$_3$O$_5$+H: 508.2811; measured: 508.2840.

PREPARATION 29

14,17-diketo-15α-methylmarcfortine A (Formula 36)

A solution of oxalyl chloride (40 µL) in anhydrous CH$_2$Cl$_2$ (5 mL) is treated with DMSO (45 µL) at –78°. The mixture is stirred for 1 h at –78°. A solution of 14α-hydroxy-15α-methyl-17-ketomarcfortine A (27 mg) in CH$_2$Cl$_2$ (2 mL) is added dropwise. The reaction mixture is stirred 20 min at –78°. Triethylamine (0.3 mL) is added to the reaction mixture which is allowed to warm to room temperature during 20 min. The mixture is partitioned between 10% Na$_2$CO$_3$ (10 mL) and CH$_2$Cl$_2$ (10 mL). The organic layer is dried (MgSO$_4$) and concentrated. The residue is subjected to silica gel chromatography (1:20 MeOH:CH$_2$Cl$_2$) to give 14,17-Diketomarcfortine A (22 mg, 80%) as a white solid. The structure of the product can be confirmed by NMR spectroscopy and mass spectrometry. HRMS (FAB) M/Z [M+H] calculated for C$_{28}$H$_{31}$N$_3$O$_6$+H: 506.2291; measured: 506.2280.

PREPARATION 30

14α-hydroxy-14β-methyl-15α-methyl-17-ketomarcfortine A (Formula 37)

A solution of 14,17-Diketo-15α-methylmarcfortine A (25 mg, 0.05 mmol) in CH$_2$Cl$_2$ (5 mL) at –78° is treated with a solution of methylmagnesium bromide (3M, 0.2 mL, 0.6 mmol) in Et$_2$O at –78°. The resulting mixture is stirred for 0.5 h at –78°. The reaction is quenched by adding 10% Na$_2$CO$_3$ (a few drops). The mixture was diluted with CH$_2$Cl$_2$ (10 mL), dried (MgSO$_4$), and concentrated. The residue is subjected to silica gel chromatography (1:25 MeOH:CH$_2$Cl$_2$) to give 14α-hydroxy-14β-methyl-15α-methyl-17-ketomarcfortine A (16 mg, 62%) as a white solid. $^1$H NMR (300 MHz, CDCl$_3$) δ8.13 (s, 1H), 6.78 (d, 1H), 6.70 (d, 1H), 6.33 (d, 1H), 4.91 (d, 1H), 3.75 (q, 2H), 3.16 (t, 1H), 3.05 (s, 3H), 2.78 (d, 1H), 2.68–2.57 (m, 1H), 2.42–2.0 (m, 6H), 1.64 (s, 3H), 1.45 (s, 3H), 1.44 (s, 3H), 1.11 (s, 3H), 1.04 (d, 3H), 0.92 (d, 3H).

PREPARATION 31

14α-hydroxy-14β-methyl-15α-methylmarcfortine A (Formula 38)

14α-Hydroxy-14β-methyl-15α-methyl-17-ketomarcfortine A (15 mg, 0.028 mmol) is dissolved in THF (10 mL) and treated with borane dimethyl sulfide complex (10M, 0.02 mL) at 0°. The mixture is stirred for 2 h at 0°, then MeOH (0.4 mL) is added and stirred for an additional 1 h. After the solvent is evaporated, the residue is subjected to silica gel chromatography (30:70 acetone:methylene chloride) to give 14α-hydroxy-14β-methyl-15α-methylmarcfortine A (4 mg, 29%) as a solid. $^1$H NMR (300 MHz, CDCl$_3$) δ7.82 (s, 1H), 6.79 (d, 1H), 6.67 (d, 1H), 6.33 (d, 1H), 4.90 (d, 1H), 3.65 (d, 1H), 3.09 (s, 3H), 2.98 (t, 1H), 2.69 (d, 1H), 2.60–2.22 (m, 7H), 2.06 (dd, 1H), 1.87 (d, 1H), 1.85–1.75 (m, 1H), 1.44 (s, 6H), 1.43 (s, 3H), 1.10 (s, 3H), 0.94 (d, 3H), 0.86 (s,3H).

Example 1

15α-Ethyl-14α-Hydroxy-17-oxomarcfortine A (II)

To copper (I) iodide (0.18 g, 0.95 mmol) in THF (10 mL) at 0° is added ethylmagnesium bromide (1M in THF, 2 mL, 2 mmol) dropwise. Following 0.25 hr of stirring at 0° the reaction is treated dropwise with 14α-hydroxy-15,16-dehydro-17-oxomarcfortine A (I, 0.1 g, 0.2 mmol) in THF (5 mL) at 0°. The reaction mixture is quenched 1 hr later with ammonium chloride (saturated, 25 mL) then extracted into ethyl acetate (2×25 mL). The combined organic extracts are dried with magnesium sulfate, filtered, and concentrated under reduced pressure to give a residue. The residue is chromatographed (silica gel; methanol/methylene chloride (4/96) to give the title compound, NMR (400 MHz, CDCl$_3$) δ7.75, 6.80, 6.70, 6.32, 4.91, 4.66, 3.75, 3.20, 3.06, 2.79, 2.09, 2.40–1.50, 1.48, 1.44, 1.11, 1.02 and 0.90 δ; MS (FAB, M/Z) [M+H]=536.

Example 2

15α-Ethyl-14α-hydroxymarcfortine A (III)

15α-Ethyl-14α-hydroxy-17-oxomarcfortine A (I, EXAMPLE 1, 40 mg, 0.075 mmol) is dissolved in THF (5 mL) and treated with borane dimethyl sulfide complex (10M, 0.08 mL, 0.8 mmol) at 0°. The mixture is stirred for 1 hr at 0° then quenched with methanol (0.2 mL) and stirred for an additional 0.25 hr at 20°–25°. The solvent is removed to give residue that is chromatography (silica gel; methanol/methylene chloride (4/96)) to give the title compound, NMR (400 MHz, CDCl$_3$) 7.85, 6.80, 6.67, 6.33, 4.90, 3.92, 3.67, 3.10, 3.01, 2.69, 1.87, 2.65–1.20, 1.45, 1.44, 1.12, 0.97 and 0.88 δ; HRMS (FAB, M/Z) [M+H] calculated for C$_{30}$H$_{39}$N$_3$O$_5$+H=522.2968, measured=522.2958.

Example 3

14α-Hydroxy-15α-vinyl-17-oxomarcfortine A (IV)

Following the general procedure of EXAMPLE 1 and making non-critical variations but using vinylmagnesium bromide (1M in THF, 39.5 mL, 0.04 mol) in place of ethylmagnesium bromide, the title compound is obtained, NMR (400 MHz, CDCl$_3$) 7.69, 6.80, 6.71, 6.32, 4.91, 6.11–5.95, 5.32–5.20, 4.50, 3.21, 3.08, 3.07–3.0, 2.80, 2.10, 2.66, 2.32, 2.20–1.80, 1.46, 1.44, 1.11 and 0.89 δ.

Example 4

14α-Hydroxy-15α-(1',2'-dihydroxyethyl)-17-oxomarcfortine A (V)

Osmium tetroxide solution (2.5/97.5) in 2-methyl-2-propanol, 1.9 mL), 4-methylmorpholine N-oxide (1.9 g, 0.016 mol) and 14α-hydroxy-15α-vinyl-17-oxomarcfortine A (IV, EXAMPLE 3, 1.9 g, 0.0035 mol) are combined and stirred for 6 hr at 20°–25° in acetone/water (9/1, 100 mL). The reaction is partitioned between water (200 mL) and methylene chloride (250 mL). The organic layer is dried over magnesium sulfate, filtered, and concentrated under reduced pressure to give residue. The residue is chromatographed (silica gel; methanol/methylene chloride (10/90)) to give the title compound. HRMS (FAB, M/Z) [M+H] calculated for $C_{30}H_{37}N_3O_8+H=568.2659$, measured=568.2670.

Example 5
14α-Hydroxy-15α-hydroxymethyl-17-oxomarcfortine A (VI)

To 14α-hydroxy-15α-(1',2'-dihydroxyethyl)-17-oxomarcfortine A (V, EXAMPLE 4, 1 g, 1.8 mmol) in ethanol (100 mL) at 0° is added sodium periodate (0.68 g in 40 mL of water) dropwise. Following 10 minutes of stirring at 0°, sodium borohydride is added and the resulting mixture is stirred an additional 10 minutes at 0°. The reaction mixture is quenched with saline (150 mL) and extracted into methylene chloride (200 mL). The organic extract is dried with magnesium sulfate, filtered, and concentrated under reduced pressure to give residue that is chromatographed (silica gel; methanol/methylene chloride (5/95)) to give the title compound. NMR (400 MHz, CDCl$_3$) 7.73, 6.81, 6.71, 6.32, 4.92, 4.72, 4.06, 3.83, 3.76, 3.21, 3.06, 2.90–2.30, 2.80, 2.10, 2.22, 2.01, 1.46, 1.44, 1.12 and 0.89 δ; MS (FAB, M/Z) [M+H]=538.

Example 6
15α-Fluoromethyl-14α-hydroxy-17-oxomarcfortine A (VII)

14α-hydroxy-15α-hydroxymethyl-17-oxomarcfortine A (VI, EXAMPLE 5, 0.06 g, 0.1 mmol), tetrabutylammonium fluoride (1M in THF, 0.66 mL, 0.66 mmol) and p-toluenesulfonyl fluoride (0.075 g, 0.43 mol) are combined and refluxed in THF (10 mL) for 0.5 hr. The mixture is cooled and concentrated. The concentrate is chromatographed (silica gel) to gave the title compound. NMR (400 MHz, CDCl$_3$) 7.93, 6.80, 6.70, 6.32, 4.90, 4.80–4.50, 4.67, 3.75, 3.21, 3.06, 2.78, 2.15, 2.70–1.50, 1.46, 1.44, 1.12 and 0.89 δ.

Example 7
15α-Fluoromethyl-14α-hydroxymarcfortine A (VII)

15α-Fluoromethyl-14α-hydroxy-17-oxomarcfortine A (VII, EXAMPLE 6, 15 mg, 0.027 mmol) is dissolved in THF (5 mL) and treated with boranetetrahydrofuran complex (1M in THF, 0.15 mL, 0.15 mmol) at 0°. The mixture is stirred for 1.5 hr at 0° then quenched with methanol (0.75 mL) and stirred for an additional 0.25 hr at 20°–25°. The solvent is removed to give a residue. The residue is chromatographed (silica gel; methanol/methylene chloride (5/95)) to give the title compound. NMR (400 MHz, CDCl$_3$) 7.57, 6.80, 6.68, 6.33, 4.90, 4.75–4.30, 4.09, 4.80, 3.50, 3.12, 3.05, 2.70, 1.88, 2.60–1.40, 1.45, 1.44, 1.12 and 0.86 δ; HRMS (FAB, M/Z) [M+H] calculated for $C_{29}H_{36}FN_3O_5+H=526.2717$, measured=526.2727.

Example 8
14,15-Dehydro-15-methylmarcfortine A (IX)

Diethylaminosulfur trifluoride (DAST, 0.15 mL, 1.1 mmol) is added dropwise at 20°–25° to 14α-hydroxy-15α-methylmarcfortine A (III, n$_1$=0, 0.2 g, 0.39 mmol) which is dissolved in methylene chloride (15 mL). Following 5 min of stirring the reaction mixture is partitioned between water (25 mL) and methylene chloride (25 mL). The organic layer is dried over magnesium sulfate, filtered, concentrated under reduced pressure, and chromatographed (silica gel) to give the title compound. NMR (400 MHz, CDCl$_3$) 7.67, 6.81, 6.68, 6.33, 4.90, 5.46, 3.66, 3.14, 3.10, 2.70, 1.88, 2.75–2.54, 2.30, 1.92, 1.78, 1.46, 1.44, 1.12 and 0.86 δ.

Example 9
14,15-Dehydro-16α-hydroxy-15-methylmarcfortine A (X)

Selenium dioxide (8 mg, 0.07 mmol) and 14,15-dehydro-15-methylmarcfortine A (IX, EXAMPLE 8, 30 mg, 0.06 mmol) are refluxed in p-dioxane for 1.5 hr. Concentration under reduced pressure followed by chromatography (silica gel) gives the title compound. NMR (400 MHz, CDCl$_3$) 7.60, 6.81, 6.69, 6.32, 4.90, 5.55, 3.75, 2.53, 3.67, 3.14, 3.10, 2.88–2.70, 2.30, 1.90, 1.95–1.50, 1.46, 1.45, 1.11, and 0.87 δ; MS (FAB, M/Z) [M+H]=506.

Example 10
14α-hydroxy-16,17-dioxo-15α-methylmarcfortine A (XI)

14α-Hydroxy-15α-methylmarcfortine A (III, 100 mg) is dissolved in dioxane/water (3/1: 20 mL) and treated with platinum on carbon (10%, 1 g). The resulting mixture is put under oxygen (using a balloon) and stirred for 16 hr at 20°–25°. After the catalyst is filtered off the solution is partitioned between sodium bicarbonate aqueous solution (10%) and methylene chloride. The organic layer is separated, dried over magnesium sulfate and concentrated. The concentrate is subjected to chromatography (silica gel; methanol/methylene chloride (5/95)). When the appropriate fractions are pooled and concentrated four compounds are obtained: (1) 14α-hydroxy-16,17-dioxo-15α-methylmarcfortine A, NMR (400 MHz, CDCl$_3$) 8.35, 6.82, 6.71, 6.32, 4.90, 4.53, 3.90, 3.76, 3.4–3.3, 3.26, 3.00, 2.80, 2.14, 2.20, 1.98, 1.45, 1.43, 1.31, 1.12 and 0.86 δ; HRMS (FAB, M/Z) [M+H] calculated for $C_2H_3N_3O_7+H=536.2397$, measured=536.2392; (2) 14α-hydroxy-16-oxo-15α-methylparaherquamide B, NMR (400 MHz, CDCl$_3$) 7.81, 6.82, 6.72, 6.33, 4.91, 4.94, 3.73, 3.53, 3.4–3.3, 3.26, 3.06, 2.82, 2.04, 2.9–2.8, 1.9–2.1, 1.46, 1.44, 1.27, 1.11 and 0.88 δ; HRMS (FAB, M/Z) [M+H] calculated for $C_{28}H_{33}N_3O_6+H=508.2447$, measured=508.2453. (3) 14α-hydroxy-17-oxo-15α-methylmarcfortine A, NMR (400 MHz, CDCl$_3$) 7.89, 6.80, 6.71, 6.32, 4.91, 4.35, 3.65, 3.20, 3.06, 2.79, 2.09, 1.9–2.5, 1.46, 1.44, 1.13, 1.12 and 0.88 δ; (4) 14α-hydroxy-16-hydroxy-17-oxo-15α-methylmarcfortine A HRMS (FAB, M/Z) [M+H] calculated for $C_{29}H_{35}N_3O_7+H=538.2553$, measured=538.2544.

Example 11
14α-hydroxy-16-oxo-15α-methylparaherquamide B (XII)

14α-Hydroxy-16,17-dioxo-15α-methylmarcfortine A (XI, EXAMPLE 10) is dissolved in methylene chloride (5 mL) and treated with m-chloroperbenzoic acid (65% pure, 30 mg). The resulting mixture is stirred at 20°–25° for 1.5 hr. The mixture is partitioned between methylene chloride (20 mL) and potassium carbonate (10%, aqueous solution, 20 mL). The organic layer is separated, dried over magnesium sulfate and concentrated. The concentrate is chromatographed (silica gel; methanol/methlene chloride (5/95)) to give the title compound. NMR (400 MHz, CDCl$_3$) NMR (400 MHz, CDCl$_3$) 7.81, 6.82, 6.72, 6.33, 4.91, 4.94, 3.73, 3.53, 3.4–3.3, 3.26, 3.06, 2.82, 2.04, 2.9–2.8, 1.9–2.1, 1.46, 1.44, 1.27, 1.11 and 0.88 δ.

Example 12
14α-Hydroxy-15α-methylparaherquamide B (XIII)

Lithium aluminum hydride (1M solution in THF, 0.21 mL) in THF (10 mL) at −60° is treated with aluminum chloride (15 mg, 3 portions). The mixture is stirred and warmed to −25° and 14α-hydroxy-16-oxo-15α-methylparaherquamide B (XII, EXAMPLE 11) is added slowly (20 mg, 2 mL in THF). The mixture is stirred at –25° for 20 min. Methanol (0.8 mL) followed by sodium cyanoborohydride (50 mg) are added to the mixture. The resulting mixture is warmed to 20°–25° and concentrated. The concentrate is partitioned between methylene chloride (20 mL) and potassium carbonate (10% aqueous solution, 20 mL). The organic layer is separated, dried over magnesium sulfate and concentrated. The concentrate is subjected to chromatography (silica gel; actone/hexane (40/60)) to give the the title compound, NMR (400 MHz, CDCl$_3$) 7.56, 6.82, 6.69, 6.32, 4.90, 4.42, 3.64, 2.62, 3.08, 3.04, 2.9–1.5, 1.46, 1.45, 1.12, 1.08 and 0.86 δ; HRMS (FAB, M/Z) [M+H] calculated for C$_{28}$H$_{35}$N$_3$O$_5$+H=494.2662, measured=494.2655.

Example 13
16,17-dioxomarcfortine A (XV), 16-oxoparaherquamide B (XVI), 15-hydroxy-16-oxoparaherquamide B, 15,16-dioxoparaherquamide B Marcfortine A (XIV, 1.1 g, 2.3 mmol) Is dissolved in dioxane/water (3/1, 150 mL) and treated with Platinum on carbon (10%, 10 g). The resulting mixture is stirred under an oxygen atmosphere (oxygen balloon) at 20°–25° for 48 hr. The catalyst is filtered off and the resulting mixture is partitioned between methylene chloride and water. The organic phase is separated, dried over magnesium sulfate, filtered, and evaporated under reduced pressure to give a residue. The residue is chromatographed (silica gel; acetone/methylene chloride, 30/70) to give:

(1) 16,17-dioxomarcfortine A, NMR (400 MHz, CDCl$_3$) 7.69, 6.81, 6.74, 6.32, 4.92, 3.95, 3.80, 3.32, 3.15, 3.14–2.70, 2.19–1.86, 1.47, 1.45, 1.12 and 0.88 δ;

(2) 16-oxoparaherquamide B, NMR (400 MHz, CDCl$_3$) 7.81, 6.80, 6.71, 6.32, 4.91, 3.74, 3.52, 3.29, 3.08, 3.0–2.85, 2.80, 2.00, 2.55–2.49, 2.08–1.75, 1.46, 1.44, 1.10 and 0.88 δ; HRMS (FAB, M/Z [M+H]) calculated for C$_{27}$H$_{31}$N$_3$O$_5$+H=478.2342, measured=478.2384;

(3) 15-hydroxy-16-oxoparaherquamide B, NMR is complicated by the diastereomers. HRMS (FAB M/Z [M+H]) calculated for C$_{27}$H$_{31}$N$_3$O$_6$+H=494.2291, measured=494.2292;

(4) 15,16-dioxoparaherquamide B, NMR (400 MHz, CDCl$_3$) 7.60, 6.83, 6.74, 6.32, 4.92, 4.12, 3.84–3.70, 3.46, 3.14, 2.89, 2.13, 2.50, 2.25, 1.95, 1.47, 1.45, 1.11 and 0.90 δ; HRMS (FAB M/Z [M+H]) calculated for C$_{27}$H$_{29}$N$_3$O$_6$+H=: 492.2134, measured=492.2141.

Example 14
14,15-Dehydro-16-oxoparaherquamide B (XVII)

A mixture of lithium diisopropylamide which is prepared from n-butyl lithium (1.6M in hexane, 1.2 mmol, 0.78 mL) and diisopropylamine (1.3 mmol, 0.17 mL) in THF (4 mL) is cooled to –60°. A mixture of 16-oxo-paraherquamide B (XVI, EXAMPLE 13, 0.15 g, 0.3 mmol) in THF (1.5 mL) is added dropwise and the reaction mixture was allowed to warm to –20° during 0.25 h. 2 The mixture is treated dropwise with phenylselenyl chloride (0.075 g, 0.39 mmol) in THF (1 mL), then quenched 5 min later with saturated sodium bicarbonate (20 mL). The reaction mixture is extracted into methylene chloride (30 mL), dried over magnesium sulfate, filtered and concentrated under reduced pressure to give a solid which is used without further purification. This material is dissolved in THF (8 mL) and treated with hydrogen peroxide (30%, 0.12 mL) at 0°. The cooling bath Is removed and the reaction mixture stirred for 0.25 hr at 20°–25°. The reaction is quenched with sodium hydroxide (1N, 10 mL), extracted into methylene chloride (30 mL), dried over magnesium sulfate, filtered, concentrated under reduced pressure and subjected to chromatography (silica gel; methanol/methylene chloride, 5/95) to give the title compound, NMR (400 MHz, CDCl$_3$) 7.78, 7.36, 6.25, 6.81, 6.70, 6.32, 4.91, 3.96, 3.60, 3.36, 3.09, 2.88, 2.09, 2.36, 1.56, 1.46, 1.45, 1.06 and 0.88 δ; HRMS (FAB, M/Z) [M+H] calculated for C$_{27}$H$_{29}$N$_3$O$_5$+H=476.2185, measured=476.2195.

Example 15
14α-Hydroxy-15α-methyl-2-desoxomarcfortine A (XXI)

To 14α-hydroxy-15α-methyl-17-oxomarcfortine A (XIX, 21 g, 0.04 mol) in THF (1.3 L) at 0° is added borane dimethyl sulfide complex (12M, 40 mL, 0.48 mol) dropwise. The resulting mixture is stirred for 2.5 hr at 0° then quenched with methanol (50 mL) slowly dropwise. The solvent is removed under reduced pressure to give a residue that is subjected to chromatography (silica gel; methanol/methylene chloride, 3/97) to give 14α-hydroxy-15α-methylmarcfortine A and 14α-hydroxy-15α-methyl-2-desoxomarcfortine A, NMR (400 MHz, CDCl$_3$) δ6.66, 6.40, 6.29, 4.79, 3.92, 3.41, 3.78, 3.55, 2.92, 2.62, 2.35, 2.25, 2.26, 2.15, 2.10–1.40, 1.40, 1.04, 1.02, 0.89, 0.91; HRMS (FAB, m/z) [M+H] calculated for C$_{29}$H$_{39}$N$_3$O$_4$+H=494.3019, measured=494.3208.

Example 16
2-Desoxomarcfortine A (XXIII)

To marcfortine A (XXII, 0.16 g, 0.335 mmol) in THF (25 mL) at 0° is added alane-N,N-dimethylethylamine complex (0.5M, 2.6 mL, 13.4 mmol) dropwise. The resulting mixture is stirred for 1 hr at 0° then quenched with methanol (5 mL) slowly dropwise. The solvent is then removed under reduced pressure to give residue that was subjected to chromatography (silica gel; acetone/methylene chloride, 30/70) to give the title compound, NMR (400 MHz, CDCl$_3$) δ6.67, 6.40, 6.29, 4.79, 3.91, 3.40, 3.57, 2.36, 2.95, 2.30–2.05, 1.95–1.25, 1.39, 0.88, 0.85; CMR (CDCl$_3$, 100 MHz) δ175.40, 146.26, 143.77, 139.74, 137.06, 126.78, 120.11, 114.88, 114.19, 79.67, 63.66, 61.13, 61.05, 60.74, 56.23, 54.68, 45.77, 41.92, 32.15, 31.94, 31.83, 30.30, 26.28, 26.19, 23.38, 21.13, 19.75; HRMS (FAB, m/z) [M+H] calculated for C$_{28}$H$_{37}$N$_3$O$_3$+H=464.2913, measured=464.2929.

Example 17
C-2-deoxoparaherquamide A

To paraherquamide A (0.05 g, 0.1 mmol) in tetrahydrofuran (THF, 6 mL) at 20°–25° under a nitrogen atmosphere is added alane-N,N-dimethylamine complex (0.5M in toluene, 2 mL, 1 mmol) dropwise. The resulting reaction mixture is stirred for 0.5 hr then quenched with methanol (1 mL). The mixture is concentrated under reduced pressure to give residue that is purified by chromatography (silica gel; acetone/methylene chloride (30/70)) to give the title compound, NMR (400 MHz, CDCl$_3$) 6.69, 6.30, 4.80, 3.94, 3.51, 3.39, 3.19, 2.92, 2.53, 2.38–2.12, 2.08, 1.95–1.74, 1.65, 1.43, 0.92 & 0.89 δ; HRMS (FAB, M/Z [M+H] calculated for C$_{28}$H$_{37}$N$_3$O$_4$+H=480.2862, measured=480.2869.

Example 18
N(1)-Phenoxycarbonylmarcfortine A (XXVII)

Marcfortine A (XXVI, 2.4 g, 5.0 mmol) in THF (120 mL) and potassium hydride (35 weight %, 0.7 g, 6.2 mmol) are stirred for 1 hr at 20°–25°. To this mixture phenylchloro formate (1.2 mL, 9.6 mmol) is added. The mixture is stirred for 0.5 hr, quenched with potassium carbonate solution (10%, 50 mL) and extracted into ethyl acetate (150 mL). The organic layer is dried over magnesium sulfate, filtered, and concentrated. The residue is triturated with ether/hexane and the precipitate is filtered, collected and dried to give the title compound as a solid, NMR (400 MHz, CDCl$_3$) 0.89, 1.08, 1.2–3.0, 1.45, 1.49, 3.06, 3.69, 4.83, 6.26, 6.89 and 7.2–7.5 δ; HRMS (FAB, m/z) [M+H] calculated for C$_{35}$H$_{39}$N$_3$O$_6$+H$^+$=598.2917, measured=598.2919.

Example 19
N(1)-tert-Butoxycarbonylmarcfortine A (XXVII)

Marcfortine A (XXVI) in THF/methylene chloride (50 mL/50 mL) and potassium hydride (35 weight %, 0.62 g, 5.5 mmol) are stirred for 1 hr at 20°–25°. To this mixture di-tert-butyl dicarbonate (3.4 g, 15.6 mmol) is added. The mixture is stirred for 0.5 hr, quenched with potassium carbonate solution (10%, 50 mL) and extracted into ethyl acetate (150 mL). The organic layer is separated and dried over magnesium sulfate, filtered, and concentrated. The concentrate is triturated with ether/hexane and the precipitate is filtered, collected and dried to give the title compound, NMR (400 MHz, CDCl$_3$) 0.83, 1.05, 1.2–3.0, 1.46, 1.53, 1.59, 3.12, 3.67, 4.85, 6.28 and 6.82 δ; HRMS (FAB, m/z) [M+H] calculated for C$_{35}$H$_{43}$N$_3$O$_6$C+H$^+$= 578.3230, measured=578.3230.

Example 20
N(1)-4'-Nitrophenoxycarbonylmarcfortine A (XXVII)

Following the general procedure of EXAMPLES 18 and 19 and making non-critical variations but using 4-nitrophenylchloro formate (423 mg, 2.1 mmol), the title compound is obtained, NMR (400 MHz, CDCl$_3$) 0.89, 1.08, 1.2–3.0, 1.45, 1.49, 3.06, 3.69, 4.83, 6.26, 6.92, 7.50 and 8.33 δ; HRMS (FAB, m/z) [M+H] calculated for C$_{35}$H$_{38}$N$_4$O$_8$+H$^+$=643.2767, measured=643.2766.

Example 21
N(1)-9'-Fluorenylmethyloxycarbonylmarcfortine A (XXVII)

Following the general procedure of EXAMPLES 18–20 and making non-critical variations but using 9-fluorenylmethyl chloroformate (1.6 g, 6 m mol), the title compound is obtained, selected NMR (400 MHz, CDCl$_3$) 7.78, 7.66, 7.42, 6.89, 6.20, 4.82, 4.70–4.60, 4.39, 3.16, 2.85, 1.45 and 1.43 δ; MS (FAB, m/z) [M+H]=700.

Example 22
N(1)-tert-Butoxycarbonylparaherquamide A (XXVII)

Paraherquamide A (XXV, 70 mg, 0.14 mmol) in THF (10 mL) and potassium hydride (35 weight %, 0.062 g, 0.55 mmol) are stirred for 2 hr at 20°–25°. To this mixture di-tert-butyl dicarbonate (86 mg, 0.42 mmol) is added. The mixture is stirred for 0.5 hr, quenched with 10% potassium carbonate solution (50 mL), and extracted into ethyl acetate (150 mL). The organic layer is dried over magnesium sulfate, filtered and concentrated. The concentrate is purified by preparative thin layer chromatography (methanol/methylene chloride, 5/95) to give the title compound, NMR (400 MHz, CDCl$_3$) 0.89, 1.02, 1.42, 1.46, 1.59, 1.63, 1.2–3.3, 3.06, 3.69, 4.83, 6.26 and 6.80 δ.

Example 23
N(1)-4'-Nitrophenoxycarbonylparaherquamide A (XXVII)

Following the general procedure of EXAMPLE 22 and making non-critical variations but using 4-nitrophenylchloroformate (814 mg, 4.2 mmol), the title compound is obtained, NMR (400 MHz, CDCl$_3$) 0.85, 0.94, 1.2–3.9, 1.40, 1.47, 3.02, 4.79, 5.85, 6.18, 6.88, 7.35 and 8.29 δ; HRMS (FAB, m/z) [M+H] calculated for C$_{35}$H$_{38}$N$_4$O$_9$+H$^+$=659.2717, measured=659.2732.

Example 24
N(1)-4'-Nitrophenoxycarbonyl-14α-hydroxy-14β-methylmarcfortine A (XXVII)

14α-Hydroxy-14β-methylmarcfortine A (XXVI, n=2, R$_{14}$=Me, R$_{15}$=H, R$_{16}$=OH, 0.188 g, 0.37 mmol) in THF (30 mL) and sodium hydride (60 weight %, 0.075 g, 1.875 mmol) are stirred for 2 hr at 20°–25°. To this mixture 4-nitrophenylchloroformate (150 mg, 0.74 mmol) is added. The mixture is stirred for 0.5 hr, quenched with pH 7 buffer solution (15 mL) and extracted into ethyl acetate (50 mL). The organic layer is separated and dried over magnesium sulfate, filtered and concentrated to give the title compound, NMR (400 MHz, CDCl$_3$) 0.92, 1.07, 1.2–3.0, 1.44, 1.47, 1.48, 3.13, 3.67, 4.87, 6.25, 6.92, 7.50 and 8.35 δ; HRMS (FAB, m/z) [M+H] calculated for C$_{36}$H$_{42}$N$_4$O$_9$+H$^+$=673.2873, measured=673.2866.

Example 25
N(1)-4'-Nitrophenoxycarbonyl-14α-hydroxy-15α-methylmarcfortine A (XXVII)

Following the general procedures of EXAMPLES 18–24 and making non-critical variations but using 14α-Hydroxy-15α-methylmarcfortine A (XXVI, n=2, R$_{14}$=H, R$_{15}$=Me, R$_{16}$=OH, 1.98 g, 3.9 mmol) and 4-nitrophenylchloroformate (150 mg, 0.74 mmol), the title compound is obtained, NMR (400 MHz, CDCl$_3$) 0.92, 1.02, 1.09, 1.2–3.0, 1.44, 1.47, 3.14, 3.68, 3.95, 4.87, 6.24, 6.92, 7.50 and 8.34 δ; HRMS (FAB, m/z) [M+H] calculated for C$_{36}$H$_{40}$N$_4$O$_9$+H$^+$=673.2873, measured=673.2866.

Example 26
N(1)-Phenoxycarbonyl-2α-hydroxy-2-desoxomarcfortine A (XXVIII)

N(1)-Phenoxycarbonylmarcfortine A (EXAMPLE 18, 2.4 g, 4.0 mmol) is dissolved in methanol (100 mL) and treated with sodium borohydride (540 mg) at 0° for 15 min. The reaction mixture is quenched with potassium carbonate (10%, 100 mL). The resulting precipitate is dried to give the title compound, NMR (400 MHz, CDCl$_3$) 0.85, 0.92, 1.3–2.7, 1.37, 1.48, 3.06, 3.18, 3.43, 3.61, 4.75, 5.87, 6.28, 6.84 and 7.2–7.5 δ; HRMS (FAB, m/z) [M+H] calculated for C$_{35}$H$_{41}$N$_3$O$_6$+H$^+$=600.3073, measured=600.3080.

Example 27
N(1)-4'-Nitrophenoxycarbonyl-2α-hydroxy-2-desoxomarcfortine A (XXVIII)

Following the general procedure of EXAMPLE 26 and using N(1)-4'-Nitrophenoxycarbonylmarcfortine A (EXAMPLE 20, 0.5 g, 0.78 mmol) the title compound is obtained, NMR (400 MHz, CDCl$_3$) 0.82, 0.89, 1.3–2.7, 1.39, 1.47, 3.06, 3.18, 3.59, 4.78, 5.85, 6.20, 6.84, 7.36 and 8.28 δ; HRMS (FAB, m/z) [M+H] calculated for C$_{35}$H$_{40}$N$_4$O$_8$+H$^+$=645.2924, measured=649.2925.

Example 28
N(1)-9'-Fluorenylmethyloxycarbonyl-2α-hydroxy-2-desoxomarcfortine A (XXVIII)

Following the general procedure of EXAMPLE 26 and making non-critical variations but using N(1)-9'-fluorenylmethyloxycarbonylmarcfortine A (EXAMPLE 21, 30 mg, 0.043 mmol) the title compound is obtained, selected NMR (400 MHz, CDCl$_3$) 7.88–7.20, 6.72, 6.64, 6.38, 4.76, 4.28, 3.01, 2.85 and 2.60 δ.

Example 29
N(1)-4'-Nitrophenoxycarbonyl-2α-hydroxy-2-desoxoparaherquamide A (XXVIII)

Following the general procedure of EXAMPLE 26 and making non-critical variations but using N(1)-4'-Nitrophenoxycarbonylparaherquamide A (EXAMPLE 23, 1.0 g, 1.52 mmol) the title compound is obtained, NMR (400 MHz, CDCl$_3$) 0.85, 0.93, 1.3–2.7, 1.40, 1.47, 1.63, 3.02, 3.2–3.6, 4.79, 5.85, 6.18, 6.88, 7.35 and 8.28 δ; HRMS (FAB, m/z) [M+H] calculated for C$_{35}$H$_{40}$N$_4$O$_9$+H$^+$= 661.2873, measured=661.2877.

Example 30
N(1)-4'-Nitrophenoxycarbonyl-14α-hydroxy-14β-methyl-2α-hydroxy-2-desoxomarcfortine A (XXVIII)

Following the general procedure of EXAMPLE 26 and making non-critical variations but using N(1)-4'-Nitrophenoxycarbonyl-14α-hydroxy-14β-methylmarcfortine A (EXAMPLE 24, 180 mg, 0.27 mmol) the title compound is obtained, NMR (400 MHz, CDCl$_3$) 0.85, 0.91, 1.3–2.7, 1.40, 1.45, 1.48, 3.09, 3.1–3.7, 4.79, 5.88, 6.21, 6.87, 7.36 and 8.29 δ; HRMS (FAB, m/z) [M+H] calculated for C$_{36}$H$_{42}$N$_4$O$_9$+H$^+$=675.3030, measured=675.3031.

Example 31
N(1)-4'-Nitrophenoxycarbonyl-14α-hydroxy-15α-methyl-2α-hydroxy-2-desoxomarcfortine A (XXVIII)

Following the general procedure of EXAMPLE 26 and making non-critical variations but using N(1)-4'-Nitrophenoxycarbonyl-14α-hydroxy-15α-methylmarcfortine A (EXAMPLE 25, 2 g, 2.97 mmol) the title compound is obtained, NMR (400 MHz, CDCl$_3$) 0.85, 0.92, 1.01, 1.3–2.7, 1.39, 1.48, 3.05, 3.1–3.7, 4.79, 5.86, 6.19, 6.87, 7.36 and 8.29 δ; HRMS (FAB M/Z) [M+H] calculated for +H$^+$=C$_{36}$H$_{42}$N$_4$O$_9$; 675.3030 measured= 675.3036.

Example 32
1,2-Dehydromarcfortine A (XIX)
Method A.

N(1)-Phenoxycarbonyl-2α-hydroxy-2-desoxomarcfortine A (XXVIII, EXAMPLE 26, 1 g, 1.67 mmol) is dissolved in glyme (15 mL) and treated with sodium hydroxide (1N, 20 mL). The mixture is refluxed for 1–2 hr. After the mixture is cooled to 20°–25°, potassium carbonate (10%, 60 mL) is added. The resulting precipitate is collected and dried to give the title compound, NMR (400 MHz, CDCl$_3$) 0.67, 1.25, 1.3–2.7, 1.44, 1.47, 3.04, 3.70, 4.91, 6.48, 6.95 and 8.18 δ; HRMS (FAB M/Z) [M+H] calculated for C$_{28}$H$_{35}$N$_3$O$_3$+H$^+$=462.2756, measured= 462.2762.

Method B.

N(1)-4'-Nitrophenoxycarbonyl-2α-hydroxy-2-desoxomarcfortine A (XXVIII, EXAMPLE 27, 50 mg, 0.08 mmol) is dissolved in glyme (1 mL), and treated with sodium hydroxide (1N, 1 mL). The mixture is stirred for 1 hr at 20°–25°. After potassium carbonate (10%, 5 mL) is added to the mixture, this is extracted into ethyl acetate (20 mL). The organic layer is separated and dried over magnesium sulfate and concentrated to give the title compound.

Method C.

To N(1)-9'-fluorenylmethyloxycarbonyl-2α-hydroxy-2-desoxomarcfortine A (XXVIII, EXAMPLE 28, 30 mg, 0.043 mmol) in DMF (3 mL) at 20°–25° is added tetrabutylammonium fluoride (1.0M in THF, 0.04 mL, 0.04 mmol) dropwise. Following 10 min of stirring the reaction mixture is quenched with potassium carbonate (10%, 30 mL) and extracted into ethyl acetate (30 mL). The organic extract is dried over magnesium sulfate, filtered and concentrated to give the residue which is chromatographed (silica gel; methanol/methylene chloride, 5/95) to give the title compound.

Example 33
1,2-Dehydroparaherquamide A (XXIX)

Following the general procedures of EXAMPLE 32, methods A and B and making non-critical variations but using N(1)-4'-nitrophenoxycarbonyl-2α-hydroxy-2-desoxoparaherquamide A (XXVIII, EXAMPLE 29, 880 mg, 1.33 mmol) the title compound is obtained, NMR (400 MHz, CDCl$_3$) 0.69, 1.22, 1.3–2.7, 1.43, 1.45, 1.66, 2.97, 3.22, 3.62, 4.90, 6.29, 6.94 and 8.13 δ; HRMS (FAB M/Z) [M+H] calculated for C$_{28}$H$_{35}$N$_3$O$_4$+H$^+$=478.2705, measured= 478.2717.

Example 34
1,2-Dehydro-14α-hydroxy-14β-methylmarcfortine A (XXIX)

Following the general procedures of EXAMPLE 32, methods A and B and making non-critical variations but using N(1)-4'-Nitrophenoxycarbonyl-14α-hydroxy-15α-methyl-2α-hydroxy-2-desoxomarcfortine A (XXVIII, EXAMPLE 31, 150 mg, 0.22 mmol) the title compound is obtained, NMR (400 MHz, CDCl$_3$) 0.68, 1.21, 1.3–2.7, 1.44, 1.46, 1.47, 3.05, 3.65, 4.91, 6.46, 6.93, and 8.19 δ.

Example 35
1,2-Dehydro-14α-hydroxy-15α-methylmarcfortine A (XXIX)

Following the general procedures of EXAMPLE 32, methods A and B and making non-critical variations but using N(1)-4'-nitrophenoxycarbonyl-14'-hydroxy-15α-methyl-2α-hydroxy-2-desoxomarcfortine A (XXVIII, EXAMPLE 31, 2 g, 2.96 mmol) the title compound is obtained, NMR (400 MHz, CDCl$_3$) 0.69, 1.04, 1.24, 1.3–2.7, 1.45, 1.47, 3.02, 3.69, 3.85, 4.92, 6.48, 6.95 and 8.19 δ.

Example 36
2-Desoxomarcfortine A (XXIV)
Method A.

1,2-Dehydromarcfortine A (XXIV, EXAMPLE 32, 220 mg, 0.48 mmol) is dissolved in methanol (10 mL) and treated with sodium borohydride (30 mg) at 0° for 15 min. The reaction mixture is quenched with potassium carbonate (10%, 20 mL). The resulting precipitate is dried to give the title compound, NMR (400 MHz) is same as that of EXAMPLE 16.

Method B.

N(1)-tert-Butoxycarbonylmarcfortine A (XXVII, EXAMPLE 19, 100 mg, 0.17 mmol) is dissolved in diglyme (5 mL) and treated with sodium borohydride (20 mg) at 20°–25°. The mixture is then heated to reflux for 0.5 hr. After the mixture is cooled to 20°–25°, potassium carbonate (10%, 10 mL) is added. The resulting precipitate is dried to give the title compound.

Example 37
2-Desoxoparaherquamide A (XXX)
Method A.

1,2-Dehydroparaherquamide A (XXIX, EXAMPLE 33, 1.5 g, 3.14 mmol) is dissolved in methanol (30 mL) and treated with sodium borohydride (250 mg) at 0° for 15 min. The reaction mixture is quenched with potassium carbonate (10%, 60 mL) and extracted into ethyl acetate (100 mL). The organic extract is dried over magnesium sulfate, filtered and concentrated to give the residue which is chromatographed (silica gel; methanol/methylene chloride, 5/95) to give the title compound. NMR (400 MHz) is same as that of EXAMPLE 17.

Method B.

N(1)-tert-Butoxycarbonylparaherquamide A (XXVII, EXAMPLE 22, 30 mg, 0.05 mmol) is dissolved in glyme (2 mL) and treated with sodium borohydride (20 mg) at 20°–25°. The mixture is then heated to reflux for 4 hr. After the mixture is cooled to 20°–25°, potassium carbonate (10%, 5 mL) is added, and extracted into ethyl acetate (10 mL). The organic layer is dried over magnesium sulfate, filtered and concentrated to give the residue which is chromatographed (silica gel; methanol/methylene chloride, 5/95) to give the title compound.

Method C.

To paraherquamide A (XXVI, 1 g, 2 mmol) in THF (distilled from benzophenone and potassium metal, 40 mL) under a nitrogen atmosphere is added sodium hydride (60% in oil, 0.24 g, 6 mmol) in one portion. The resulting reaction mixture is stirred for 0.75 hr at 20°–25°, cooled to 0° and treated with 9-fluorenylmethylchloroformate (0.8 g, 3 mmol) in one portion. The reaction is quenched 5 minutes later with a phosphate buffer solution (pH=7, purchased from EM Science, 40 mL) diluted with water (40 mL) and extracted into ethyl acetate (2×50 mL). The combined organic extracts are dried over magnesium sulfate, filtered and concentrated under reduced pressure to give the crude N(1)-9'-fluorenylmethyloxycarbonylparaherquamide A (XXVII, 1.4 g, 2 mmol) which is dissolved in methanol, cooled to 0° and treated with sodium borohydride (0.3 g, 7.9 mmol) in one portion. The reaction is quenched 10 minutes later with sodium bicarbonate (saturated, 100 mL) and extracted into ethyl acetate (2×50 mL). The combined organic extracts are dried over magnesium sulfate, filtered and concentrated under reduced pressure to give the crude N(1)-9'-fluorenylmethyloxycarbonyl-2α-hydroxy-2-desoxoparaherquamide A (XXVIII, 1.4 g, 2 mmol) which is dissolved in THF (50 mL) at 20°–25° and treated with tetrabutylammonium fluoride (1.0M in THF, 8 mL, 8 mmol). Following 0.5 hr of stirring, the reaction mixture is quenched with water (50 mL) and extracted into ethyl acetate (2×50 mL). The combined organic extracts are dried over magnesium sulfate, filtered and concentrated under reduced pressure to give 1,2-dehydroparaherquamide A (XXIX, 0.96 g, 2 mmol). This compound is dissolved in methanol at 0° and treated with sodium borohydride (0.5 g, 13 mmol) in one portion. The reaction is quenched 10 minutes later with sodium bicarbonate (saturated aqueous solution, 100 mL) and extracted into ethyl acetate (2×50 mL). The combined organic extracts are dried over magnesium sulfate, filtered, concentrated under reduced pressure and chromatographed (silica gel; acetone/methylene chloride, 30/70) to give the title compound.

Example 38

2-Desoxo-14α-hydroxy-14β-methylmarcfortine A (XXX)

Following the general procedure of EXAMPLE 38 (method A) and making non-critical variations but using 1,2-dehydro-14α-hydroxy-14β-methylmarcfortine A (XXIX, EXAMPLE 34, 50 mg, 1 mmol) the title compound is obtained, NMR (400 MHz, CDCl₃) 0.86, 0.90, 1.3–2.7, 1.42, 1.46, 2.94, 3.40, 3.52, 3.93, 4.79, 6.29, 6.39 and 6.66 δ; HRMS (FAB M/Z) [M+H] calculated for $C_{29}H_{39}N_3O_4$+ $H^+$=494.3018, measured=494.3018.

Example 39

2-Desoxo-14α-hydroxy-15α-methyl-2α-hydroxy-2-desoxomarcfortine A (XXX)

Following the general procedure of EXAMPLE 37 (method A) and making non-critical variations but using 1,2-dehydro-14α-hydroxy-15α-methylmarcfortine A (XXIX, EXAMPLE 35, 1.0 g, 2.0 mmol) the title compound is obtained, NMR (400 MHz) is same as that of EXAMPLE 15.

Example 40

2β-Methyl-2-desoxomarcfortine A (XXXI)

1,2-Dehydromarcfortine A (XXIX, EXAMPLE 32, 42 mg, 0.09 mmol) is dissolved in THF (10 mL) and treated with methyl lithium (lithium bromide complex, 1.5M in ether, 0.06 mL) at −78° for 15 min. The mixture is warmed to 20°–25° and quenched with potassium carbonate (10%, 5 mL) and extracted into ethyl acetate (20 mL). The organic extract is dried over magnesium sulfate, filtered and concentrated to give a residue that is chromatographed (silica gel; methanol/methylene chloride, 5/95) to give the title compound, NMR (400 MHz, CDCl₃) 0.81, 0.92, 1.17, 1.3–2.7, 1.41, 1.43, 3.02, 3.63, 3.95, 4.79, 6.29, 6.38 and 6.63 δ; HRMS (FAB M/Z) [M+H] calculated for $C_{29}H_{39}N_3O_3$+$H^+$=478.3069, measured=478.3083.

CHART A

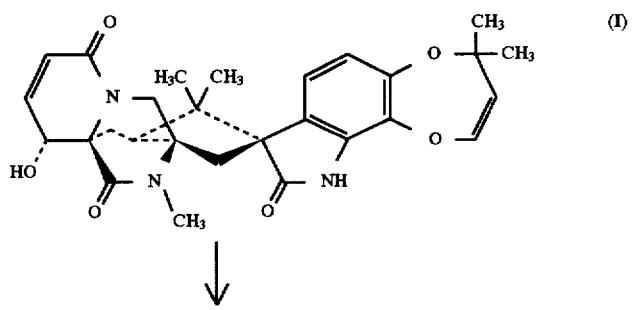

-continued
CHART A
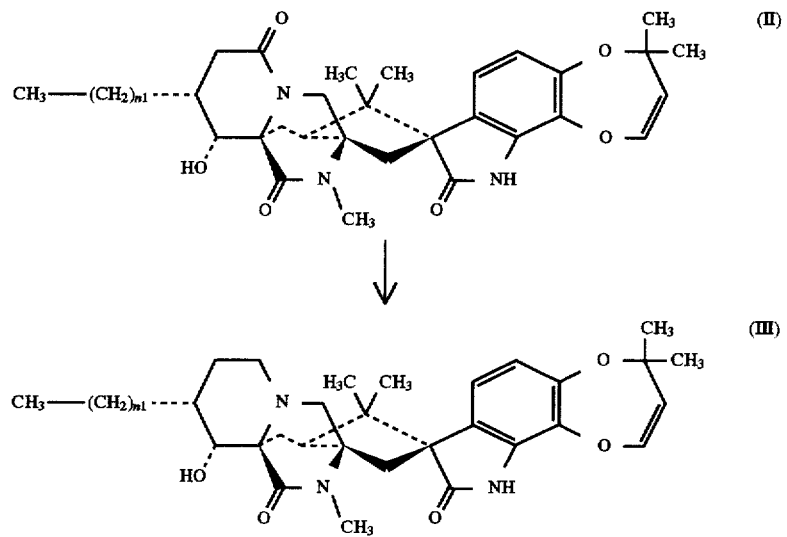
CHART B
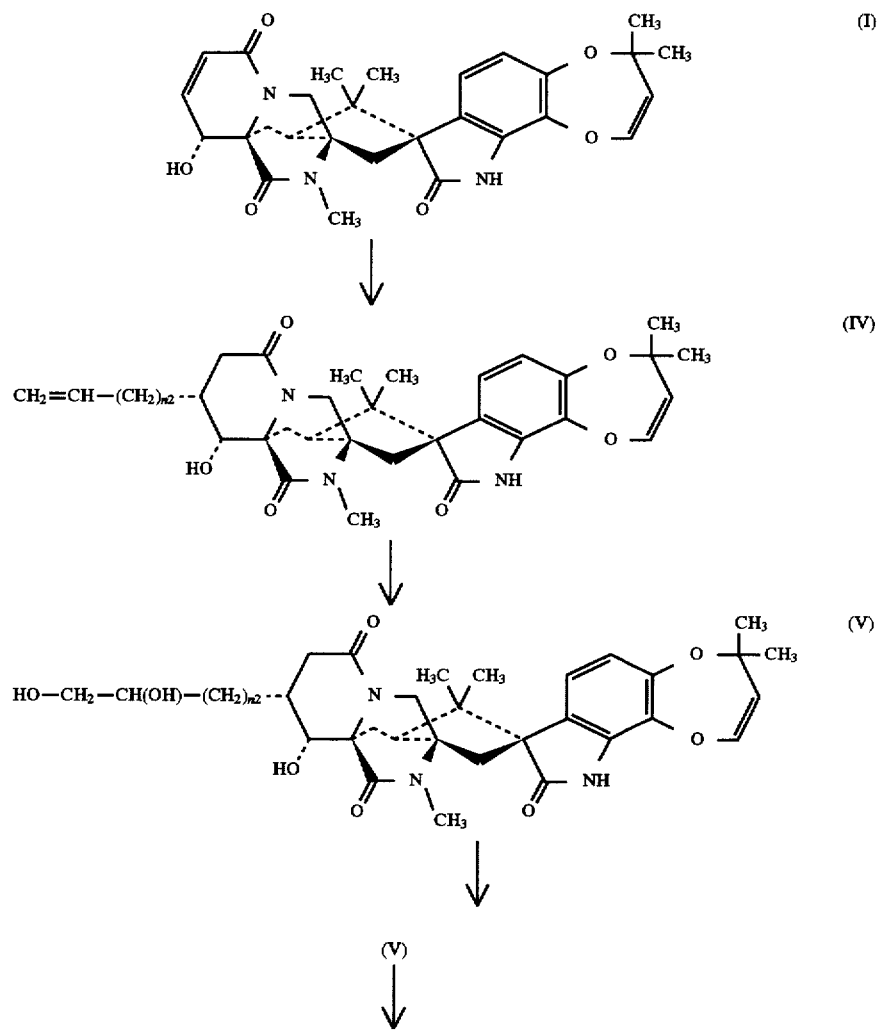

-continued
CHART B
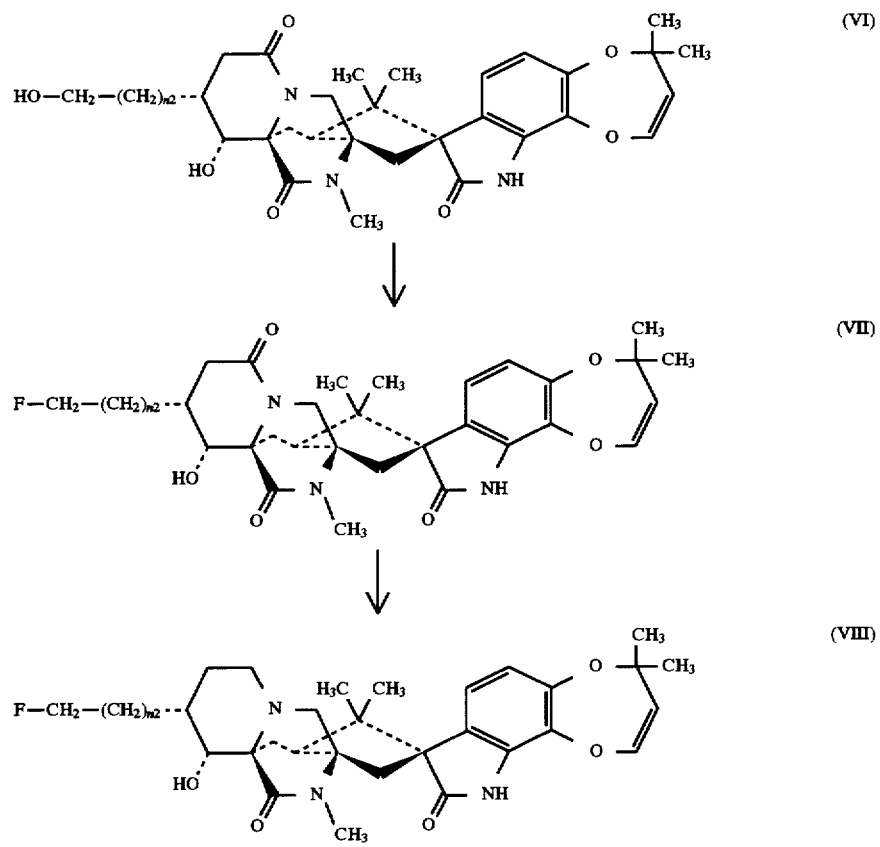
CHART C
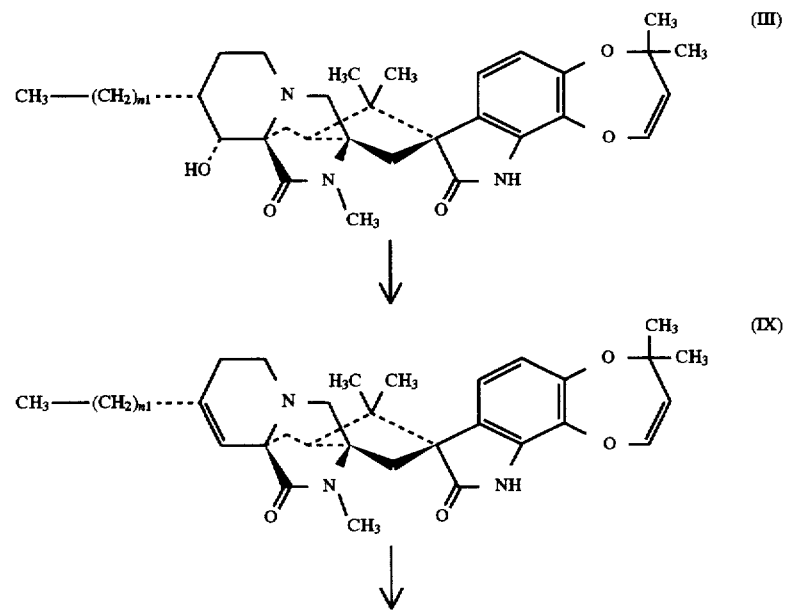

-continued
CHART C
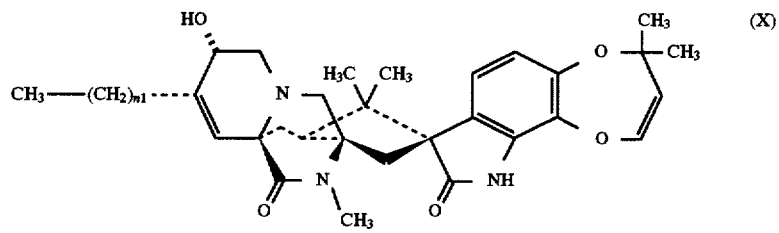
CHART D
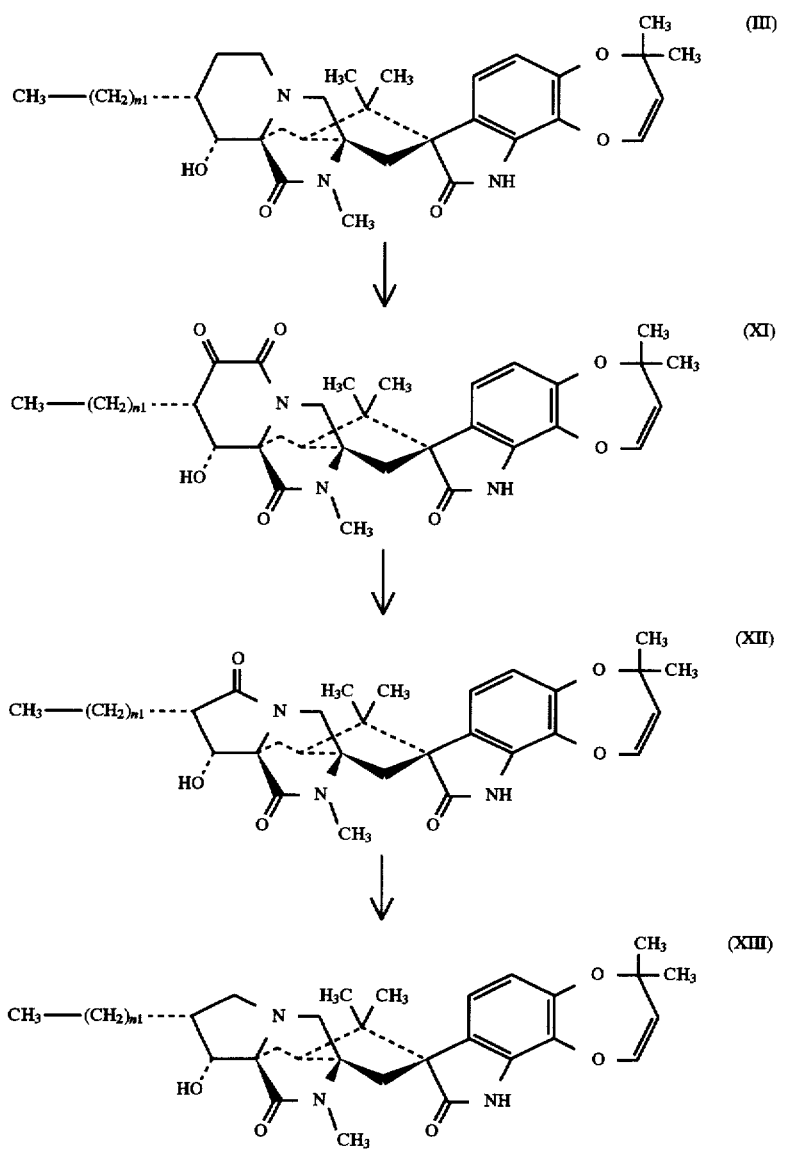

CHART F
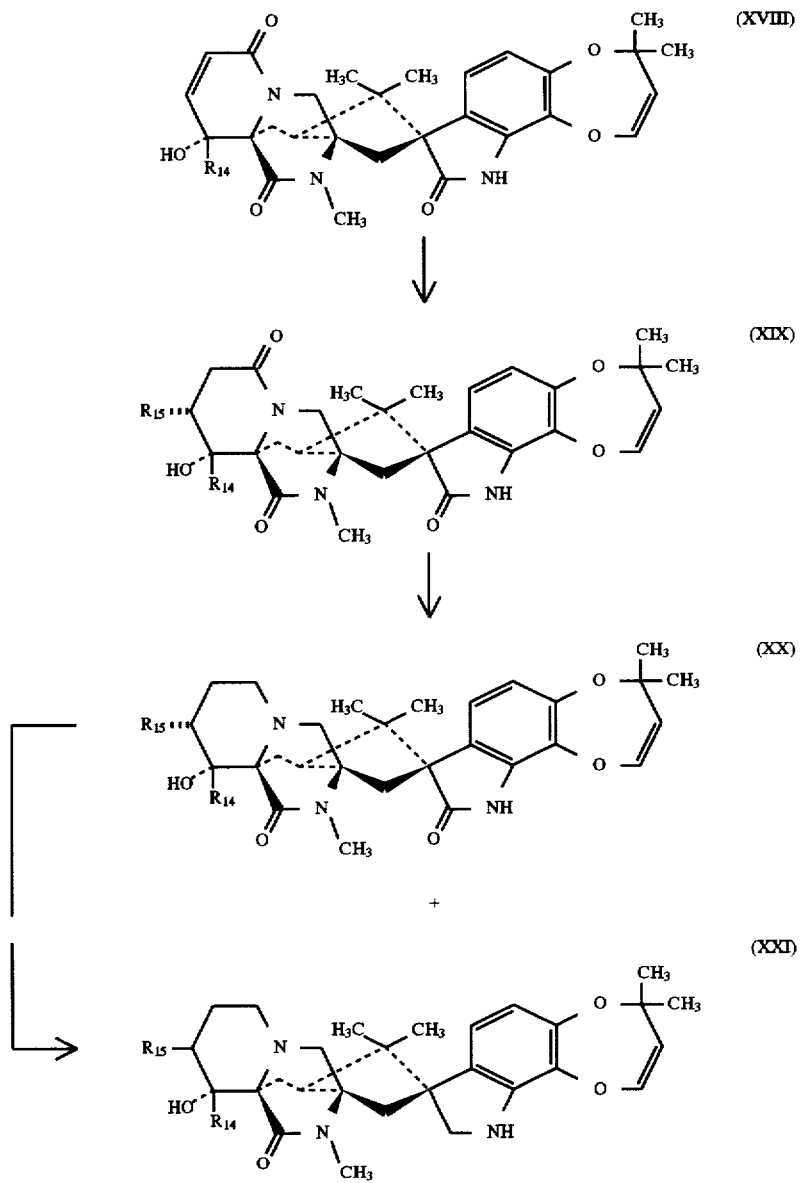
CHART G
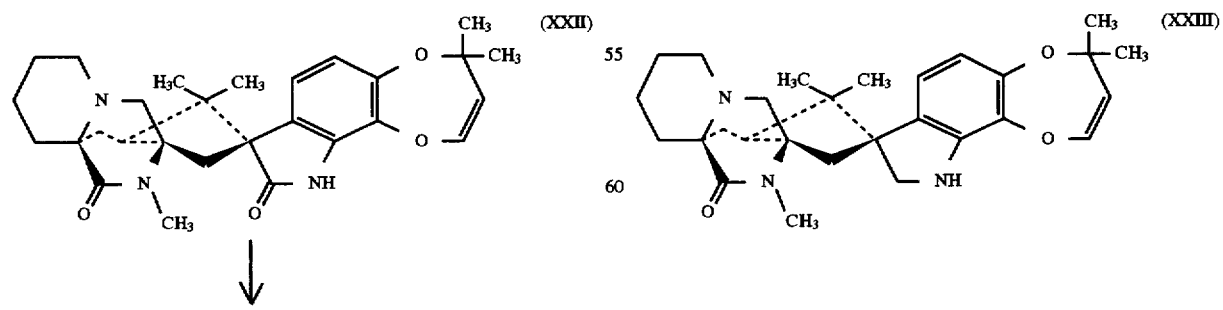

CHART H
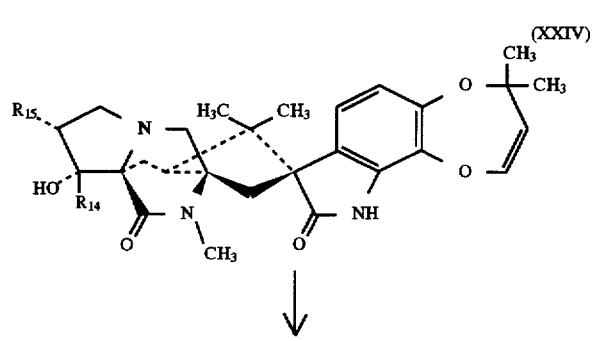
(XXIV)
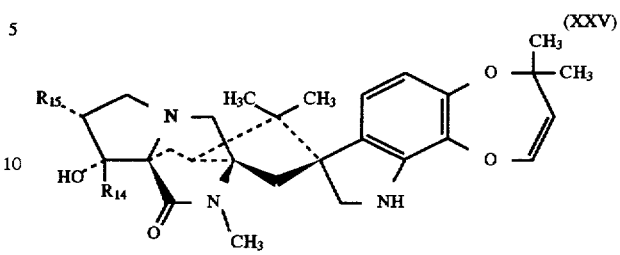
(XXV)
CHART I
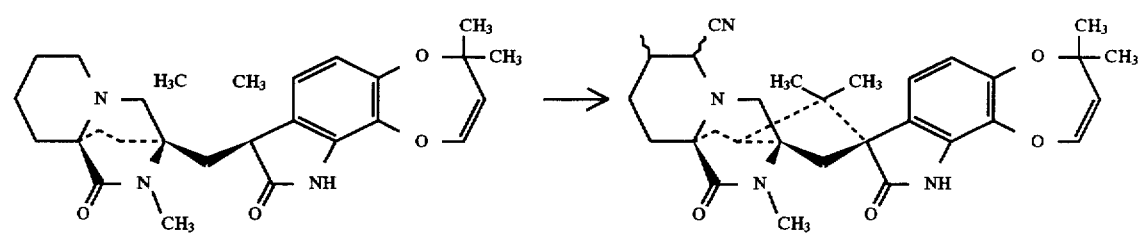
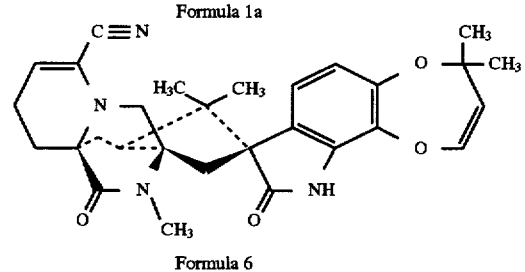
Formula 1a
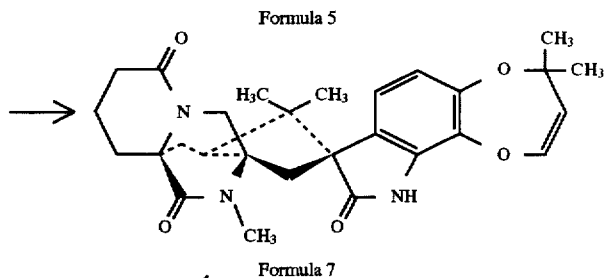
Formula 5
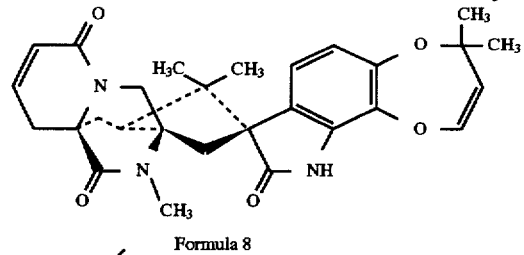
Formula 6
Formula 7
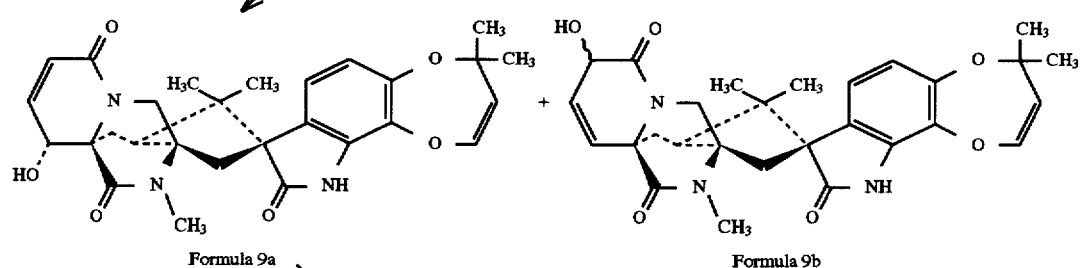
Formula 8
Formula 9a
Formula 9b -continued
CHART I
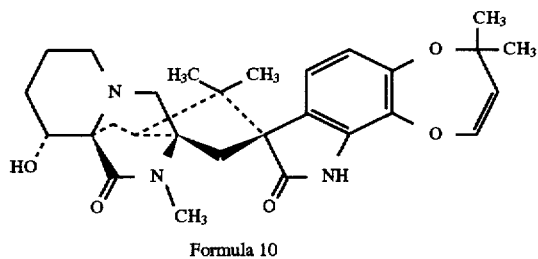
Formula 10
CHART J
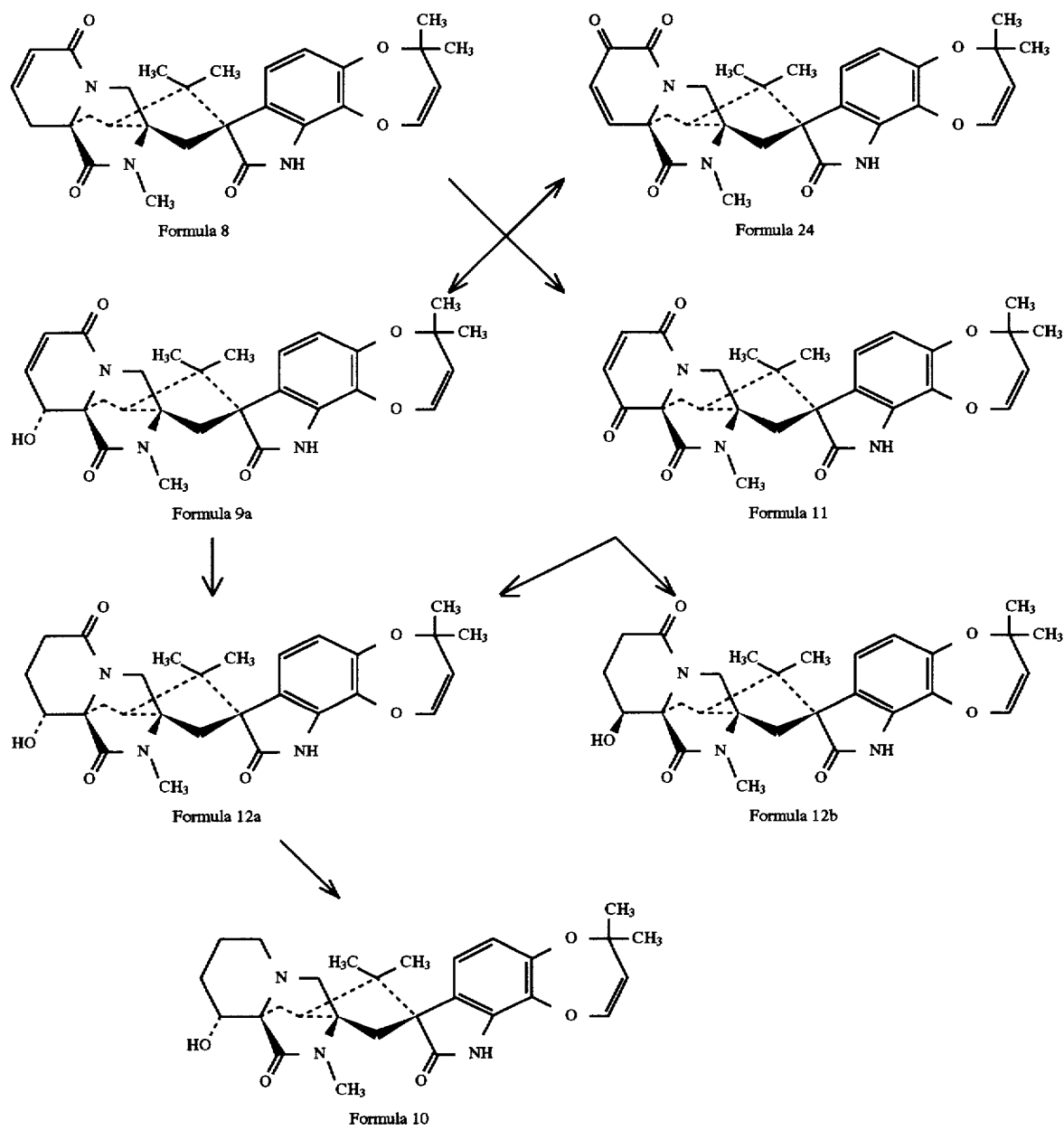

CHART K
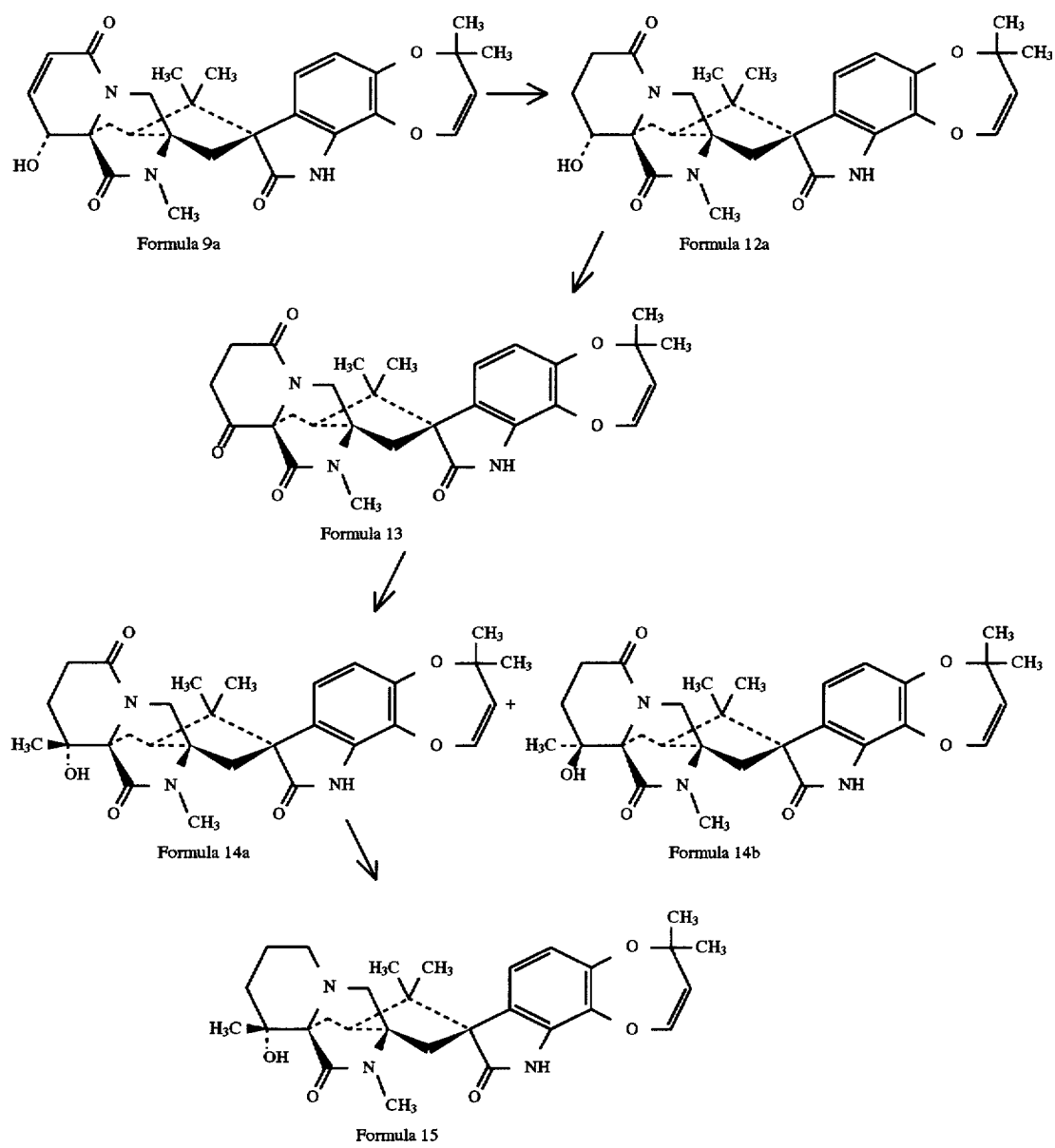

CHART L
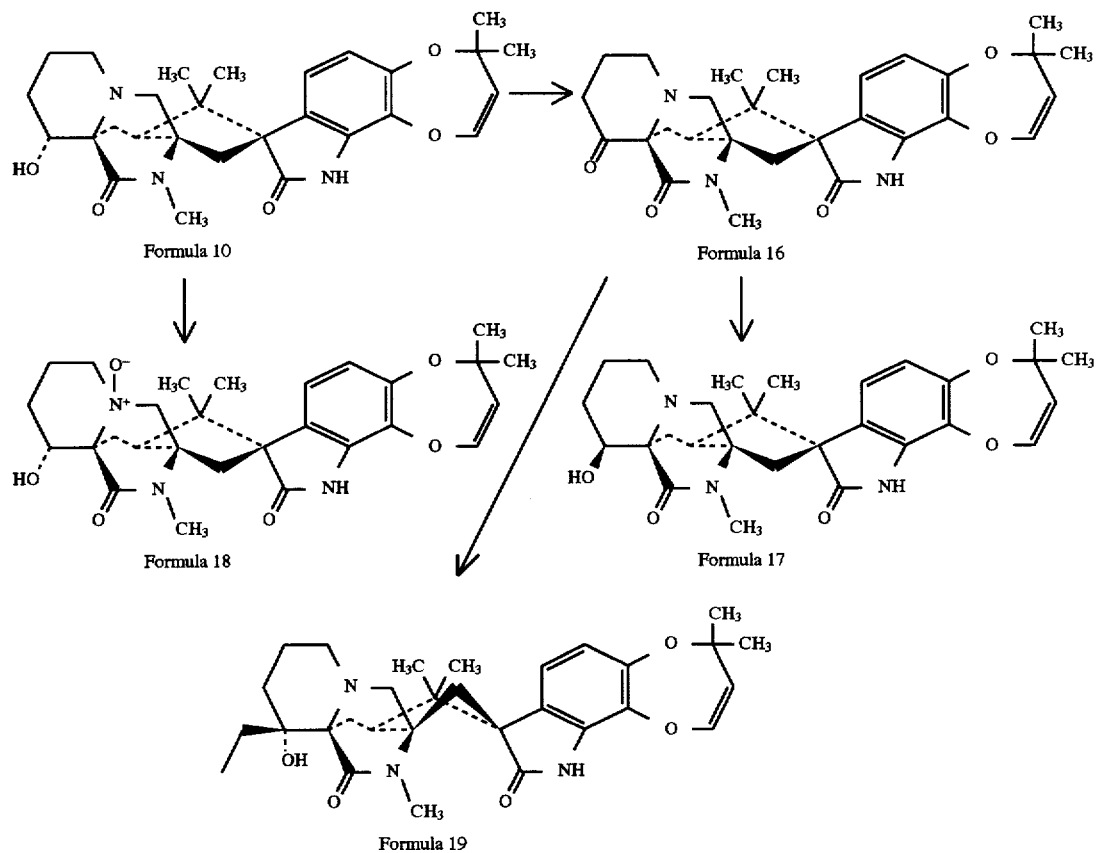
CHART M
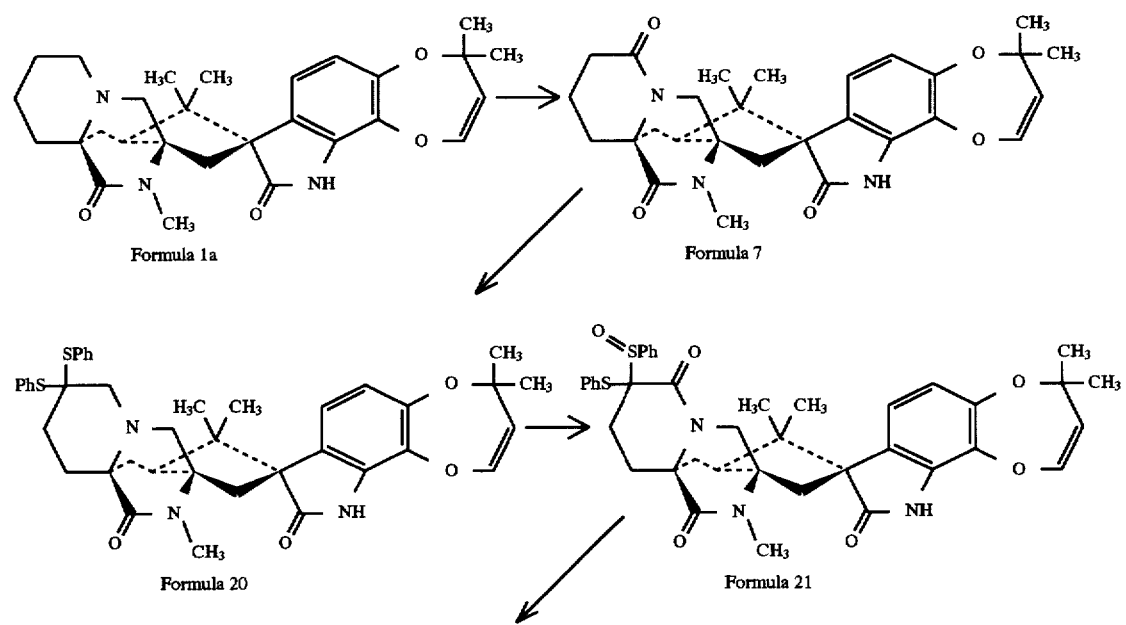

-continued
CHART M
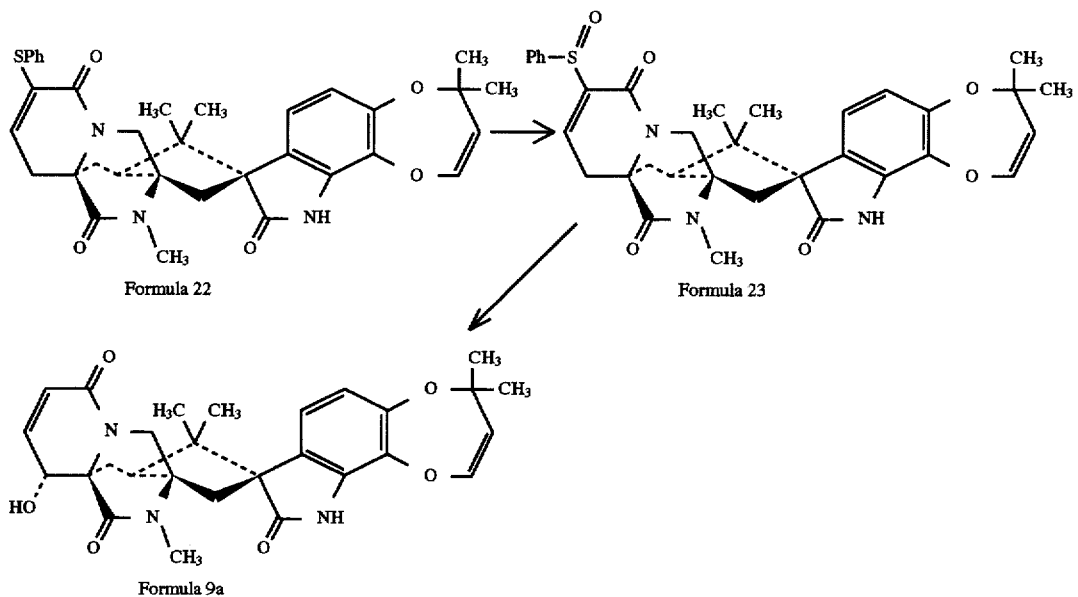
CHART N
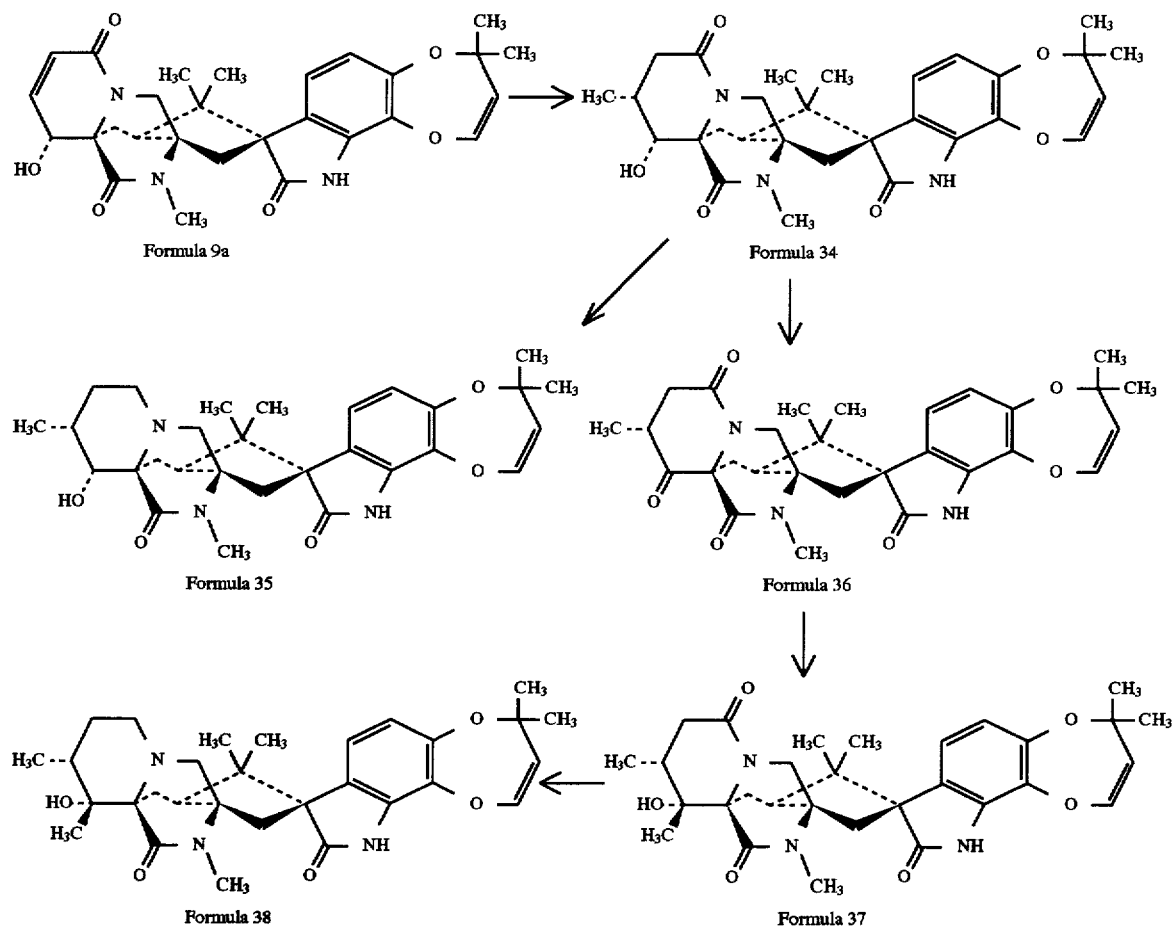

CHART O

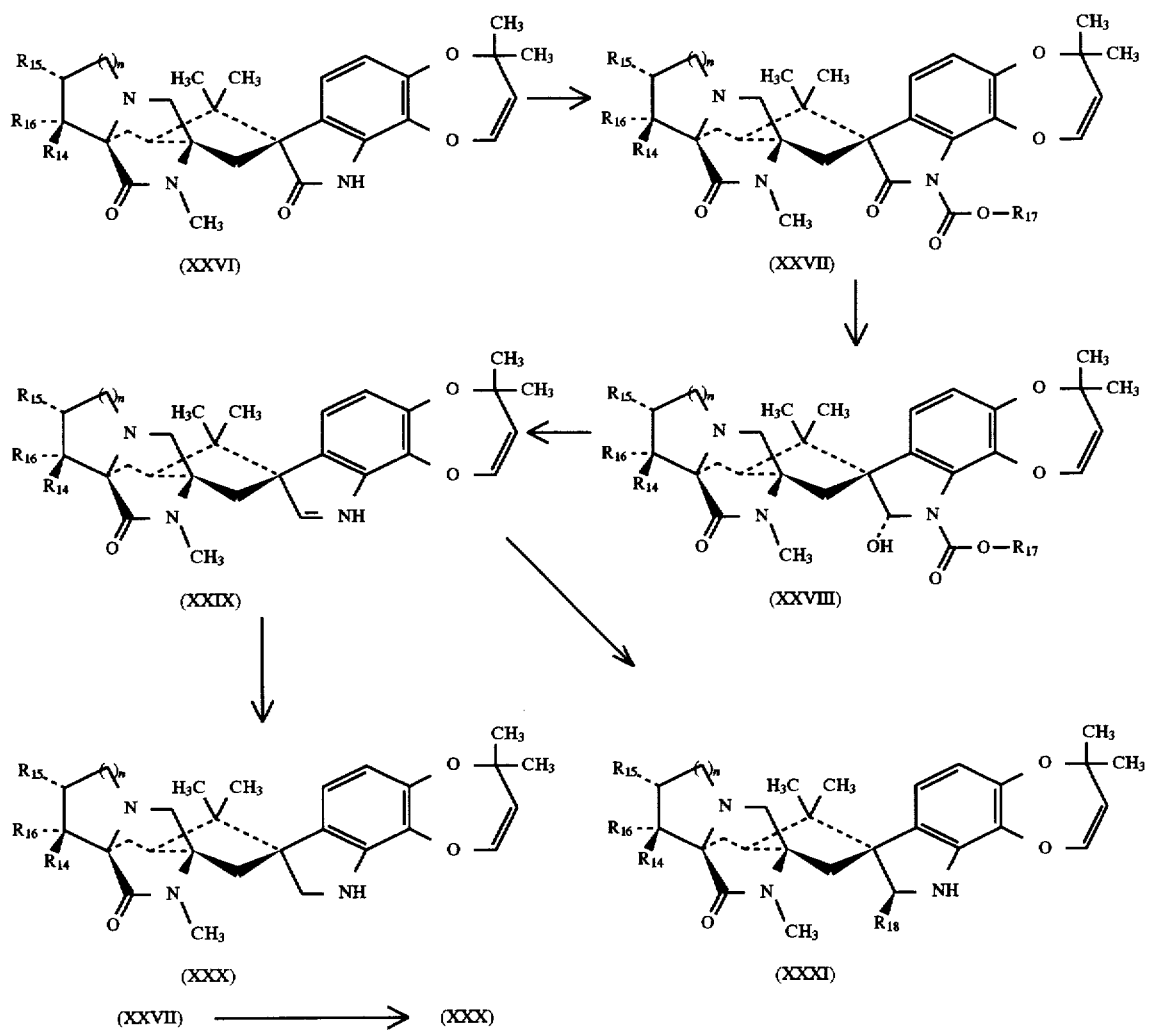

We claim:
1. 14,15-Dehydro-16-oxoparaherquamide B.
2. 14-Hydroxy-2-deoxoparaherquamide B of formula (XXV)

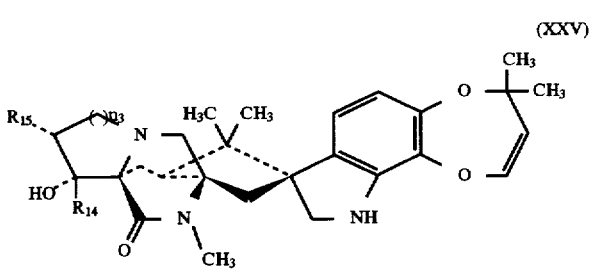

where $n_3$ is 1;
where $R_{14}$ is —H or $C_1$-$C_4$ alkyl;
where $R_{15}$ is —H or $C_1$-$C_4$ alkyl; the N-oxides and pharmaceutically acceptable salts thereof.
3. A 14-hydroxy-2-deoxoparaherquamide compound of formula (XXV) according to claim 2 where the pharmaceutically acceptable salts are salts selected from the group consisting of the acids methanesulfonic, hydrochloric, hydrobromic, sulfuric, phosphoric, nitric, benzoic, citric, tartaric, fumaric, maleic, $CH_3$—$(CH_2)_n$—COOH where n is 0 thru 4, HOOC—$(CH_2)_n$—COOH where n is as defined above.
4. A 14-hydroxy-2-deoxoparaherquamide compound of formula (XXV) according to claim 2 which is C-2-desoxoparaherquamide B.
5. 1,2-Dehydro compound of formula (XXIX)

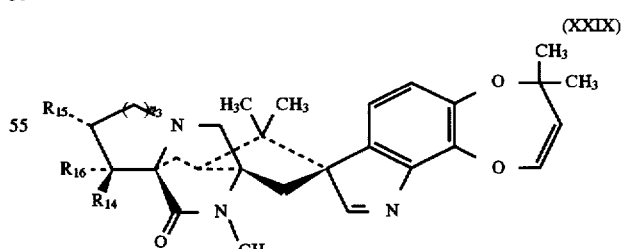

$n_3$ is 1;
where $R_{14}$ is —H and $C_1$-$C_4$ alkyl;
where $R_{15}$ is —H and $C_1$-$C_4$ alkyl;
where $R_{16}$ is —OH, the N-oxides and pharmaceutically acceptable salts thereof.
6. A 1,2-dehydro compound (XXIX) according to claim 5 where the pharmaceutically acceptable salts are salts selected from the group consisting of the acids methanesulfonic, hydrochloric, hydrobromic, sulfuric, phosphoric, nitric, benzoic, citric, tartaric, fumaric, maleic, $CH_3$—$(CH_2)_n$—COOH where n is 0 thru 4, HOOC—$(CH_2)_n$—COOH where n is as defined above.

7. A 1,2-dehydro compound (XXIX) according to claim 5 which is:

1,2-dehydroparaherquamide A.

8. 2-Alkyl-2-desoxo compound (XXXI)

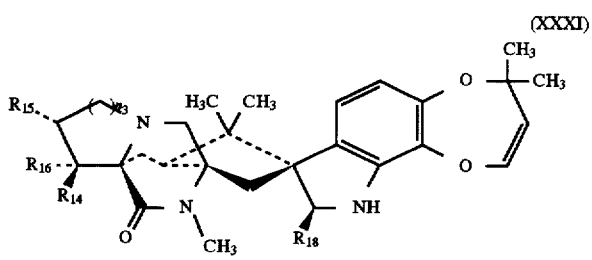

(XXXI)

where $n_3$ is 1;

where $R_{14}$ is —H and $C_1$-$C_4$ alkyl;

where $R_{15}$ is —H and $C_1$-$C_4$ alkyl;

where $R_{16}$ is —OH;

where $R_{18}$ is $C_1$-$C_4$ alkyl, the N-oxides and pharmaceutically acceptable salts thereof.

9. 2-Alkyl-2-desoxo compound (XXXI) according to claim 8 where the pharmaceutically acceptable salts are salts selected from the group consisting of the acids methanesulfonic, hydrochloric, hydrobromic, sulfuric, phosphoric, nitric, benzoic, citric, tartaric, fumaric, maleic, $CH_3$—$(CH_2)_n$—COOH where n is 0 thru 4, HOOC—$(CH_2)_n$—COOH where n is as defined above.

* * * * *